United States Patent
Jäckel et al.

(10) Patent No.: US 11,160,831 B2
(45) Date of Patent: Nov. 2, 2021

(54) FUSION PROTEIN FOR USE IN THE TREATMENT OF HVG DISEASE

(71) Applicants: MEDIZINISCHE HOCHSCHULE HANNOVER, Hannover (DE); TECHNISCHE UNIVERSITÄT BRAUNSCHWEIG, Braunschweig (DE)

(72) Inventors: Elmar Jäckel, Hannover (DE); Fatih Noyan, Hannover (DE); Michael Hust, Hannover (DE)

(73) Assignees: Medizinische Hochschule Hannover, Hannover (DE); Technische Universität Braunschweig, Braunschweig (DE)

( * ) Notice: Subject to any disclaimer, the term of this patent is extended or adjusted under 35 U.S.C. 154(b) by 383 days.

(21) Appl. No.: 16/310,312

(22) PCT Filed: Jun. 22, 2017

(86) PCT No.: PCT/EP2017/065472
§ 371 (c)(1),
(2) Date: Dec. 14, 2018

(87) PCT Pub. No.: WO2018/001874
PCT Pub. Date: Jan. 4, 2018

(65) Prior Publication Data
US 2019/0290691 A1 Sep. 26, 2019

(30) Foreign Application Priority Data
Jun. 30, 2016 (EP) .................... 16177208

(51) Int. Cl.
| | |
|---|---|
| C07K 14/725 | (2006.01) |
| A61K 35/17 | (2015.01) |
| A61P 37/06 | (2006.01) |
| C07K 16/28 | (2006.01) |
| C07K 19/00 | (2006.01) |
| C12N 15/85 | (2006.01) |
| A61K 39/00 | (2006.01) |

(52) U.S. Cl.
CPC .............. *A61K 35/17* (2013.01); *A61P 37/06* (2018.01); *C07K 14/7051* (2013.01); *C07K 16/2833* (2013.01); *C07K 19/00* (2013.01); *C12N 15/85* (2013.01); *A61K 2039/505* (2013.01); *C07K 2317/622* (2013.01); *C07K 2319/00* (2013.01); *C07K 2319/03* (2013.01); *C07K 2319/33* (2013.01)

(58) Field of Classification Search
None
See application file for complete search history.

(56) References Cited

FOREIGN PATENT DOCUMENTS

WO 2015/123642 A1 8/2015

OTHER PUBLICATIONS

MacDonald et al., "Alloantigen-specific regulatory T cells generated with a chimeric antigen receptor", The Journal of Clinical Investigation 1-12 (Mar. 22, 2016).
Inaguma et al., "Construction and molecular characterization of a T-cell receptor-like antibody and CAR-T cells specific for minor histocompatibility antigen HA-1H", Gene Therapy 575-584 (2014).
Noyan et al., "Isolation of human antigen-specific regulatory T cells with high suppressive function", Cancer Gene Therapy 19, 352-357 (2012).
Gala et al. "Avoiding cytotoxicity of transposases by dose-controlled mRNA delivery", Nuc. Ac. Res. 39, 7147-7160 (2011).
Distasi et al., "Inducible Apoptosis as a Safety Switch for Adoptive Cell Therapy", N Engl J Med 1673-1683 (2011).
Long et al., "Defects in IL-2R Signaling Contribute to Diminished Maintenance of FOXP3 Expression in CD4+CD25+ Regulatory T-Cells of Type 1 Diabetic Subjects", Diabetes, 407-415 (2010).
Hombach et al., "Adoptive immunotherapy with genetically engineered T cells: modification of the IgG 1 Fc 'spacer' domain in the extracellular moiety of chimeric antigen receptors avoids 'off-target' activation and unintended initiation of an innate immune response", Gene Therapy 1206-1213 (2010).
Reyes et al., "Characterization of swine leucocyte antigen alleles in a crossbred pig to be used in xenotransplant studies", Tissue Antigens 484-488 (2014).
Watkins et al., "The isolation and characterisation of human monoclonal HLA-A2 antibodies from an immune V gene phage display library", Tissue Antigens 219-228 (2000).
Elivan et al., "Amelioration of Colitis by Genetically Engineered Murine Regulatory T Cells Redirected by Antigen-Specific Chimeric Receptor", Gastroenterology 136, 1721-1731 (2009).
Siener, Eleonora, International Search Report for Application No. PCT/EP2017/065472, dated Sep. 8, 2017.

*Primary Examiner* — Zachary S Skelding
(74) *Attorney, Agent, or Firm* — Greer, Burns & Crain, Ltd.; Steven P. Fallon; E. Kate Berezutskaya

(57) ABSTRACT

The invention provides a fusion protein for use in the treatment of HvG disease in a patient having received a transplant, for use in suppressing the host's immune response directed against the transplant. The fusion protein is adapted for use in suppressing the immune rejection of a transplant which contains or expresses HLA-A*02 or SLA-01*0401 in a recipient patient who is negative for HLA-A*02 or SLA-01*0401, i.e. the patient prior to transplantation does not express HLA-A*02 or SLA-01*0401. The fusion protein is a chimeric antigen receptor (CAR), which upon expression in regulatory T-cells ($T_{reg}$) causes a specific suppressor activity of the regulatory T-cells in the presence of HLA-A*02 or SLA-01*0401.

Figure 1:
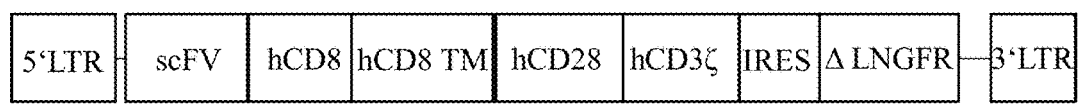
Figure 1:
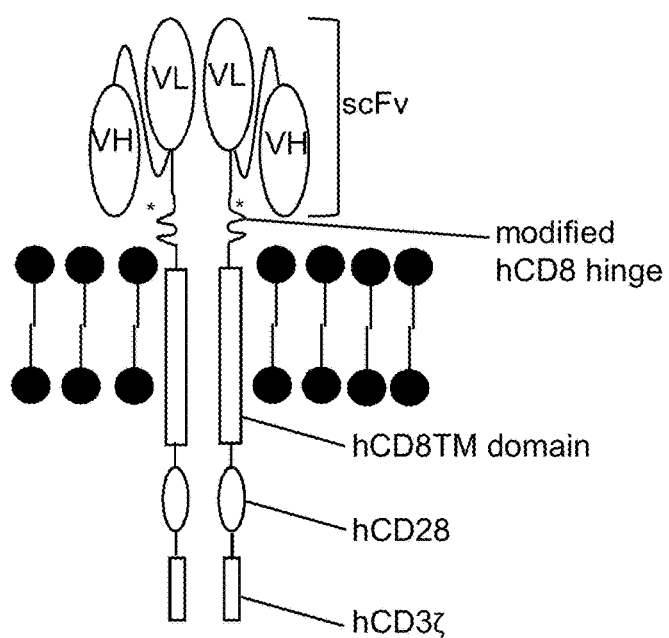

18 Claims, 20 Drawing Sheets
Specification includes a Sequence Listing.

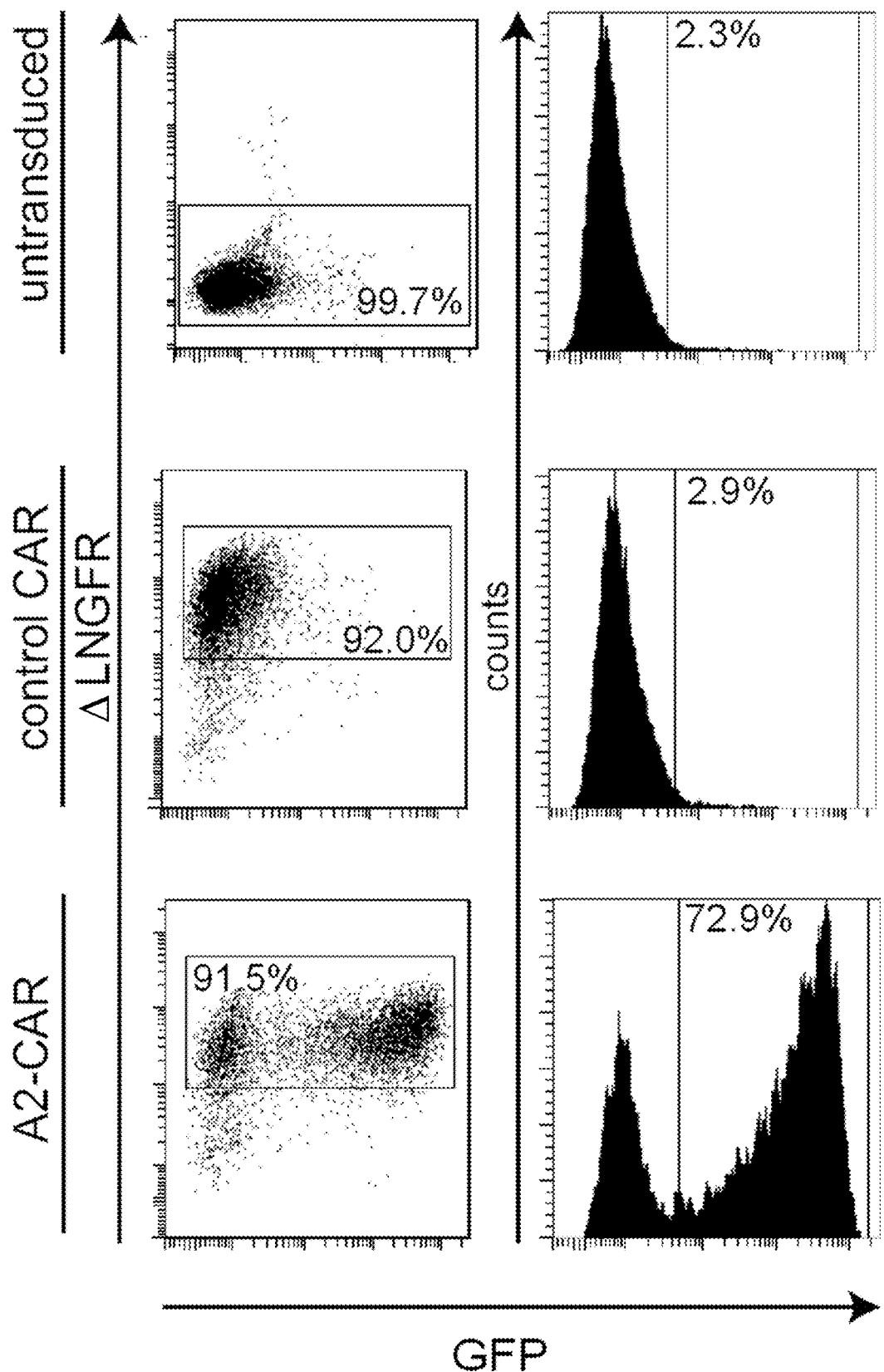
Figure 3A HLA-A*02 pos stimulator cells

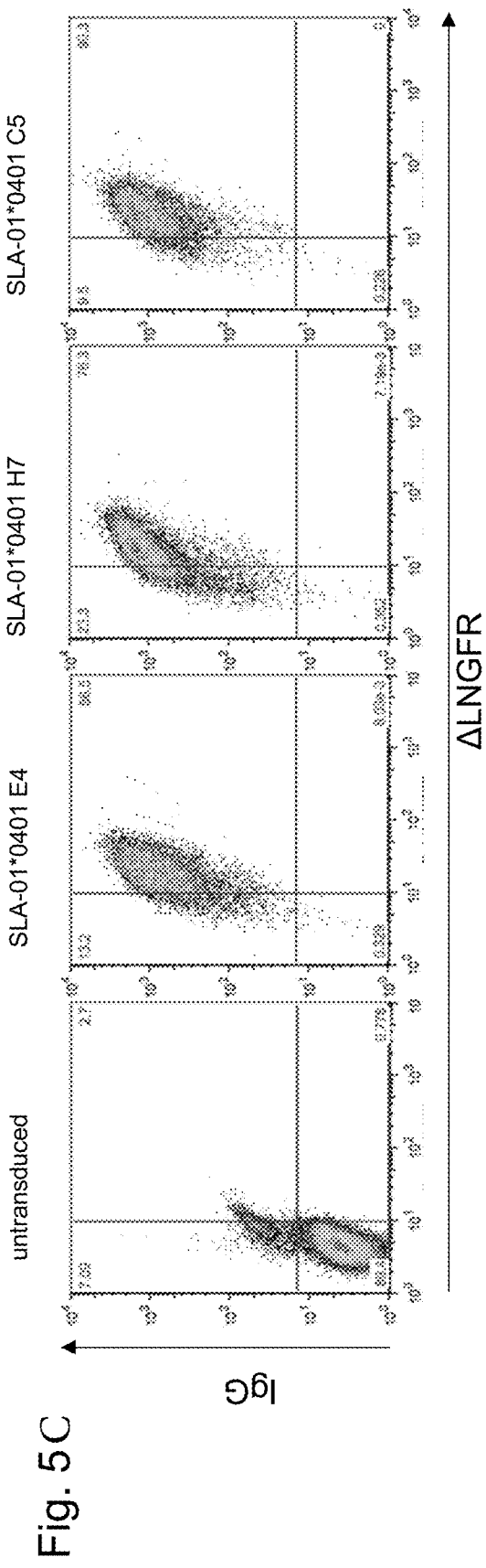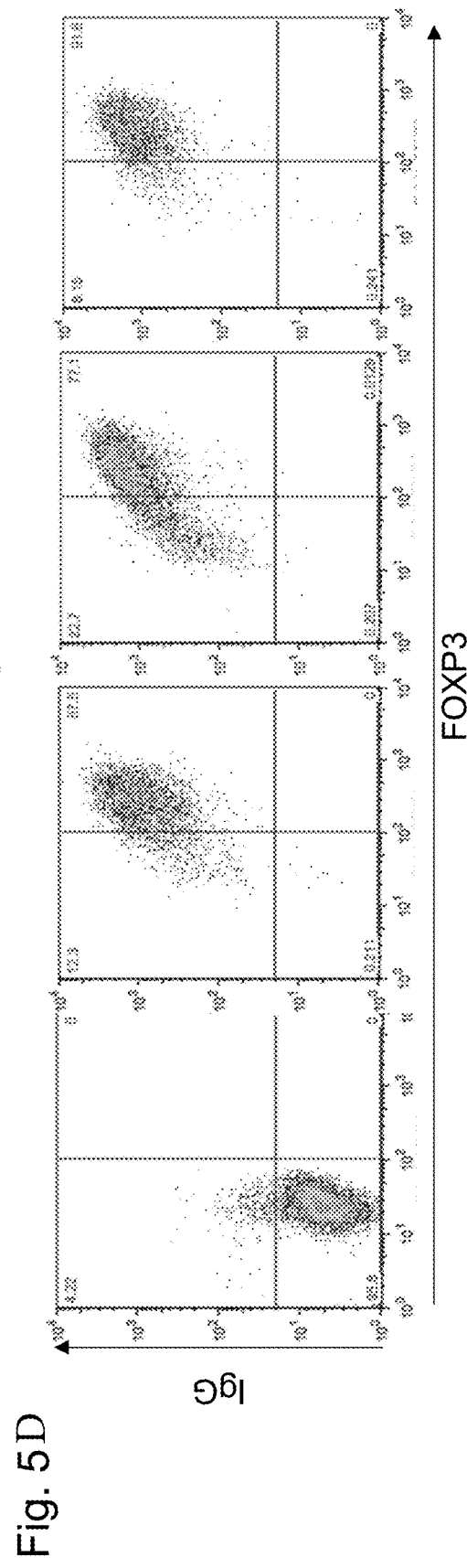
Fig. 5C
Fig. 5D

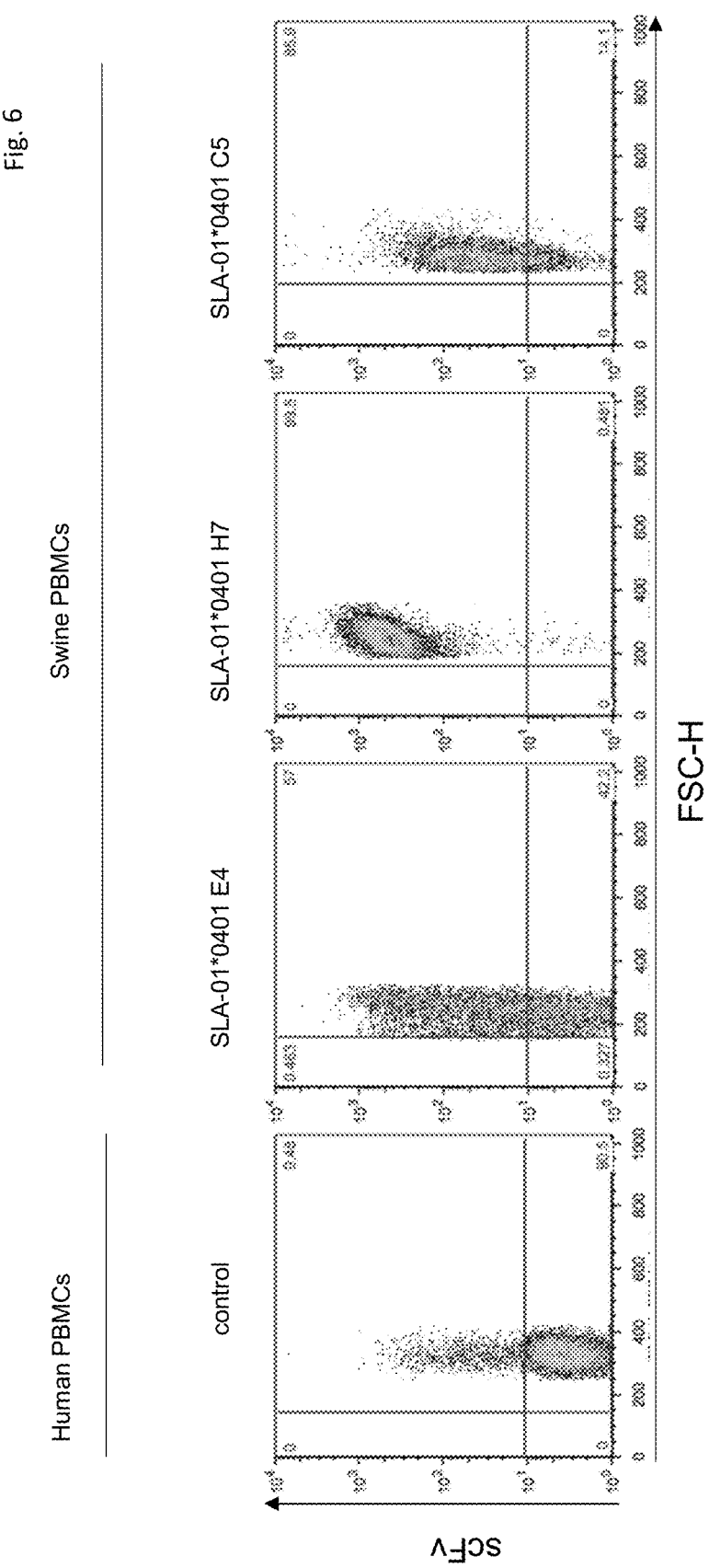

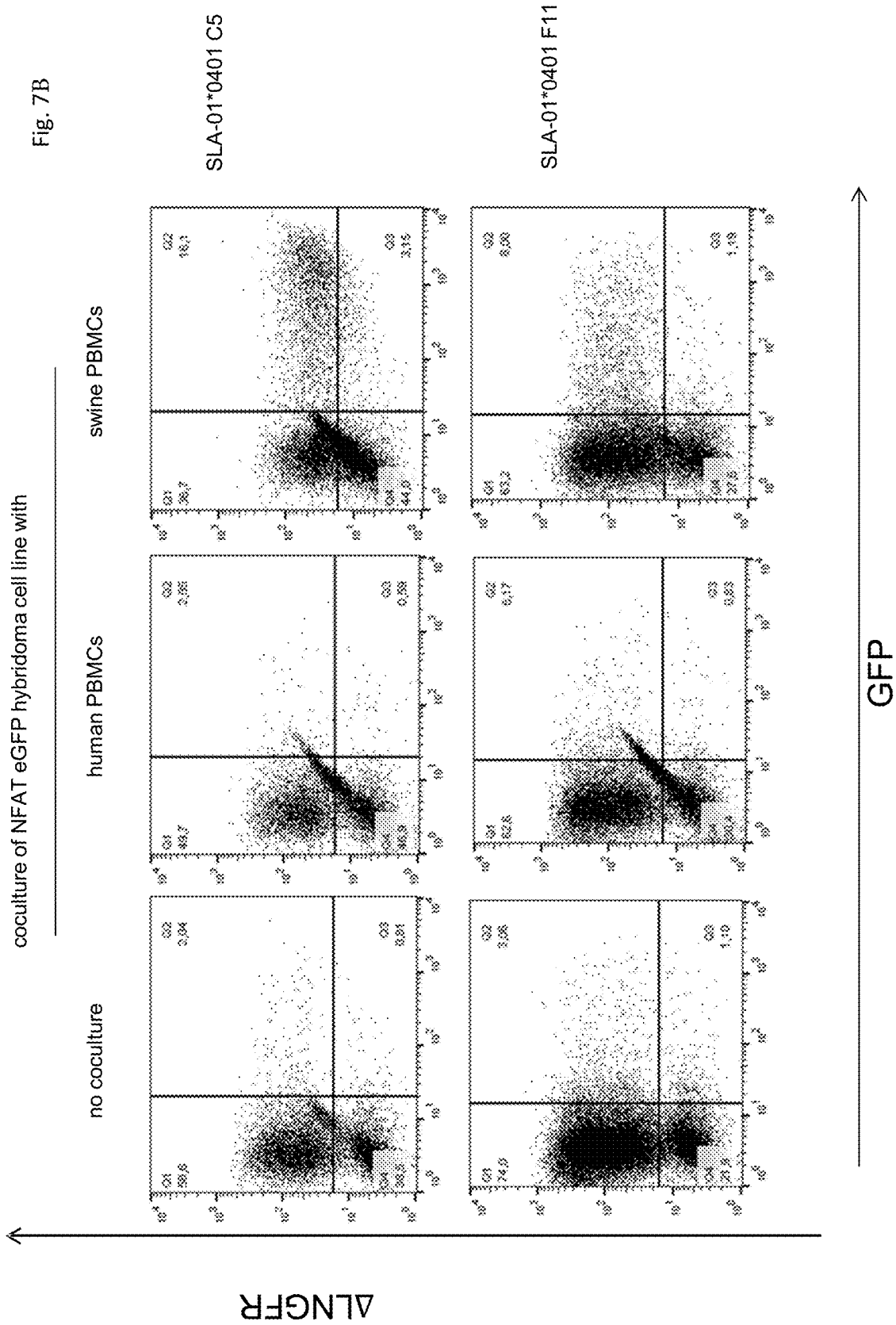

SEQUENCE LISTING

```
<160> NUMBER OF SEQ ID NOS: 25

<210> SEQ ID NO 1
<211> LENGTH: 251
<212> TYPE: PRT
<213> ORGANISM: Artificial Sequence
<220> FEATURE:
<221> NAME/KEY: CHAIN
<222> LOCATION: 1..123
<223> OTHER INFORMATION: variable heavy chain
<220> FEATURE:
<223> OTHER INFORMATION: scFv (KAZ15-C1)
<220> FEATURE:
<221> NAME/KEY: CHAIN
<222> LOCATION: 124..141
```

```
<223> OTHER INFORMATION: linker
<220> FEATURE:
<221> NAME/KEY: CHAIN
<222> LOCATION: 142..251
<223> OTHER INFORMATION: variable light chain

<400> SEQUENCE: 1

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Ser Arg Gly Ser Tyr Tyr Tyr Met Asp Val
            100                 105                 110

Trp Gly Lys Gly Thr Thr Val Thr Val Ser Ser Gly Ser Ala Ser Ala
        115                 120                 125

Pro Lys Leu Glu Glu Gly Glu Phe Ser Glu Ala Arg Val Gln Ser Val
    130                 135                 140

Leu Thr Gln Pro Pro Ser Thr Ser Gly Thr Pro Gly Gln Arg Val Thr
145                 150                 155                 160

Ile Ser Cys Ser Gly Ser Ser Asn Ile Gly Gly Asn Ala Val Asn
                165                 170                 175

Trp Tyr Gln His Phe Pro Gly Thr Ala Pro Thr Leu Leu Ile Tyr Ser
            180                 185                 190

Asn Asn Gln Arg Pro Ser Gly Val Pro Glu Arg Phe Ser Gly Ser Lys
        195                 200                 205

Ser Gly Thr Ser Ala Ser Leu Thr Val Ser Gly Leu Gln Ala Glu Asp
    210                 215                 220

Glu Ala Asp Tyr Tyr Cys Thr Ala Trp Asp Asp Ser Leu Arg Gly Tyr
225                 230                 235                 240

Leu Phe Gly Thr Gly Thr Lys Val Thr Val Leu
                245                 250

<210> SEQ ID NO 2
<211> LENGTH: 249
<212> TYPE: PRT
<213> ORGANISM: Artificial Sequence
<220> FEATURE:
<221> NAME/KEY: CHAIN
<222> LOCATION: 1..123
<223> OTHER INFORMATION: variable heavy chain
<220> FEATURE:
<223> OTHER INFORMATION: scFv (KAZ15-F3)
<220> FEATURE:
<221> NAME/KEY: CHAIN
<222> LOCATION: 124..141
<223> OTHER INFORMATION: linker
<220> FEATURE:
<221> NAME/KEY: CHAIN
<222> LOCATION: 142..249
<223> OTHER INFORMATION: variable light chain

<400> SEQUENCE: 2

Gln Val Gln Leu Val Glu Ser Gly Gly Gly Val Val Gln Pro Gly Arg
```

```
                1               5                   10                  15
            Ser Leu Arg Leu Ser Cys Ala Ala Ser Gly Phe Thr Phe Ser Ser Tyr
                               20                  25                  30
            Ala Met His Trp Val Arg Gln Ala Pro Gly Lys Gly Leu Glu Trp Val
                               35                  40                  45
            Ala Val Ile Ser Tyr Asp Gly Ser Asn Lys Tyr Ala Asp Ser Val
                               50                  55                  60
            Lys Gly Arg Phe Thr Ile Ser Arg Asp Asn Ser Lys Asn Thr Leu Tyr
            65                  70                  75                  80
            Leu Gln Met Asn Ser Leu Arg Ala Glu Asp Thr Ala Val Tyr Tyr Cys
                               85                  90                  95
            Ala Arg Asp Arg Glu Glu Leu Leu Ala Leu Phe Gly Gly Met Asp Val
                               100                 105                 110
            Trp Gly Gln Gly Thr Thr Val Thr Val Ser Ser Gly Ser Ala Ser Ala
                               115                 120                 125
            Pro Lys Leu Glu Glu Gly Glu Phe Ser Glu Ala Arg Val Gln Pro Val
                               130                 135                 140
            Leu Thr Gln Pro Ser Ser Val Ser Val Ala Pro Gly Gln Thr Ala Arg
            145                 150                 155                 160
            Ile Thr Cys Gly Gly Asn Asn Ile Gly Ser Lys Ser Val His Trp Tyr
                               165                 170                 175
            Gln Gln Lys Pro Gly Gln Ala Pro Val Leu Val Val Tyr Asp Asp Ser
                               180                 185                 190
            Asp Arg Pro Ser Gly Ile Pro Glu Arg Phe Ser Gly Ser Asn Ser Gly
                               195                 200                 205
            Asn Thr Ala Thr Leu Thr Ile Ser Arg Val Glu Ala Arg Asp Glu Ala
                               210                 215                 220
            Asp Tyr Tyr Cys His Val Trp Asp Ala Lys Thr Asn His Gln Val Phe
            225                 230                 235                 240
            Gly Gly Gly Thr Arg Leu Thr Val Gln
                               245

<210> SEQ ID NO 3
<211> LENGTH: 251
<212> TYPE: PRT
<213> ORGANISM: Artificial Sequence
<220> FEATURE:
<221> NAME/KEY: CHAIN
<222> LOCATION: 1..123
<223> OTHER INFORMATION: variable heavy chain
<220> FEATURE:
<223> OTHER INFORMATION: scFv (SH1319-A5)
<220> FEATURE:
<221> NAME/KEY: CHAIN
<222> LOCATION: 124..141
<223> OTHER INFORMATION: linker
<220> FEATURE:
<221> NAME/KEY: CHAIN
<222> LOCATION: 142..251
<223> OTHER INFORMATION: variable light chain

<400> SEQUENCE: 3

Glu Val Gln Leu Val Gln Ser Gly Ala Glu Val Lys Lys Pro Gly Ser
            1                   5                   10                  15
            Ser Val Lys Val Ser Cys Lys Ala Ser Gly Gly Thr Phe Ser Ser Tyr
                               20                  25                  30
            Ala Ile Ser Trp Val Arg Gln Ala Pro Gly Gln Gly Leu Glu Trp Met
                               35                  40                  45
            Gly Gly Ile Ile Pro Ile Phe Gly Thr Ala Asn Tyr Ala Gln Lys Phe
```

```
              50                  55                  60
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Pro Gln Ser Arg Trp Leu Gln Ser Gly Asp Ala Phe Asp Ile
                100                 105                 110

Trp Gly Gln Gly Thr Met Val Thr Val Ser Ser Gly Ala Ser Ala
                115                 120                 125

Pro Lys Leu Glu Glu Gly Glu Phe Ser Glu Ala Arg Val Gln Pro Val
                130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Gly Tyr Asn Arg Val
                165                 170                 175

Ser Trp Tyr Gln Gln Thr Pro Gly Thr Ala Pro Lys Leu Met Ile Tyr
                180                 185                 190

Glu Val Ser Asn Arg Pro Ser Gly Val Ser Asn Arg Phe Ser Gly Ser
                195                 200                 205

Lys Ser Gly Asn Thr Ala Ser Leu Thr Ile Ser Gly Leu Gln Ala Glu
                210                 215                 220

Asp Glu Ala Asp Tyr Tyr Cys Ser Ser Tyr Thr Ser Ser Ser Thr Val
225                 230                 235                 240

Val Phe Gly Gly Gly Thr Lys Leu Thr Val Leu
                245                 250
```

```
<210> SEQ ID NO 4
<211> LENGTH: 246
<212> TYPE: PRT
<213> ORGANISM: Artificial Sequence
<220> FEATURE:
<221> NAME/KEY: CHAIN
<222> LOCATION: 1..119
<223> OTHER INFORMATION: variable heavy chain
<220> FEATURE:
<223> OTHER INFORMATION: scFv (SH1313-B8)
<220> FEATURE:
<221> NAME/KEY: CHAIN
<222> LOCATION: 120..137
<223> OTHER INFORMATION: linker
<220> FEATURE:
<221> NAME/KEY: CHAIN
<222> LOCATION: 138..246
<223> OTHER INFORMATION: variable light chain

<400> SEQUENCE: 4

Gln Val Gln Leu Gln Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
                35                  40                  45

Gly Arg Ile Asn Ala Gly Asn Gly Asn Thr Lys Tyr Ser Gln Lys Phe
             50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Asp Leu Thr Gly Thr Leu Leu Phe Asp Tyr Trp Gly Gln Gly
```

```
                     100                 105                 110
Thr Leu Val Thr Val Ser Ser Gly Ser Ala Ser Ala Pro Lys Leu Glu
            115                 120                 125
Glu Gly Glu Phe Ser Glu Ala Arg Val Gln Ser Val Leu Thr Gln Pro
        130                 135                 140
Pro Ser Ala Ser Gly Thr Pro Gly Gln Arg Val Thr Ile Ser Cys Ser
145                 150                 155                 160
Gly Ser Ser Ser Asn Ile Gly Ser Asn Gly Val Lys Trp Tyr Gln Gln
                165                 170                 175
Leu Pro Gly Thr Ala Pro Lys Leu Val Ile Tyr Arg Asp Tyr Gln Arg
            180                 185                 190
Pro Ser Gly Val Pro Asp Arg Phe Ser Gly Ser Lys Ser Gly Thr Ser
        195                 200                 205
Ala Ser Leu Ala Ile Ser Gly Leu Gln Ser Glu Asp Glu Ala Lys Tyr
    210                 215                 220
Tyr Cys Ala Ala Trp Asp Asp Ser Leu Asn Val Val Phe Gly Gly Gly
225                 230                 235                 240
Thr Gln Leu Thr Val Leu
                245

<210> SEQ ID NO 5
<211> LENGTH: 251
<212> TYPE: PRT
<213> ORGANISM: Artificial Sequence
<220> FEATURE:
<221> NAME/KEY: CHAIN
<222> LOCATION: 1..123
<223> OTHER INFORMATION: variable heavy chain
<220> FEATURE:
<223> OTHER INFORMATION: scFv (SH1319-B11)
<220> FEATURE:
<221> NAME/KEY: CHAIN
<222> LOCATION: 124..141
<223> OTHER INFORMATION: linker
<220> FEATURE:
<221> NAME/KEY: CHAIN
<222> LOCATION: 142..251
<223> OTHER INFORMATION: variable light chain

<400> SEQUENCE: 5

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Ala Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Ala Glu Arg Trp Leu His Leu Ser Gly Ala Phe Asp Ile
            100                 105                 110
Trp Gly Gln Gly Thr Met Val Thr Val Ser Ser Gly Ser Ala Ser Ala
        115                 120                 125
Pro Lys Leu Glu Glu Gly Glu Phe Ser Glu Ala Arg Val Gln Pro Val
    130                 135                 140
Leu Thr Gln Ser Ser Ser Ala Ser Gly Thr Pro Gly Gln Arg Val Ala
```

```
                145                 150                 155                 160
Ile Ser Cys Ser Gly Ser Ser Asn Val Gly Ser Asn Thr Val Asn
                165                 170                 175

Trp Tyr Gln Gln Ser Pro Gly Thr Ala Pro Lys Leu Leu Ile Ser Ser
                180                 185                 190

Asn His Gln Arg Pro Ser Gly Val Pro Asp Arg Phe Ser Gly Ser Lys
                195                 200                 205

Phe Gly Thr Ser Ala Ser Leu Ala Ile Ser Gly Leu Gln Ser Glu Asp
        210                 215                 220

Glu Ala Asp Tyr Tyr Cys Gly Ala Trp Asp Ser Leu Asn Gly Tyr
225                 230                 235                 240

Val Phe Gly Ser Gly Thr Lys Val Thr Val Leu
                245                 250

<210> SEQ ID NO 6
<211> LENGTH: 244
<212> TYPE: PRT
<213> ORGANISM: Artificial Sequence
<220> FEATURE:
<221> NAME/KEY: CHAIN
<222> LOCATION: 1..116
<223> OTHER INFORMATION: variable heavy chain
<220> FEATURE:
<223> OTHER INFORMATION: scFv (SH1319-C5)
<220> FEATURE:
<221> NAME/KEY: CHAIN
<222> LOCATION: 117..134
<223> OTHER INFORMATION: linker
<220> FEATURE:
<221> NAME/KEY: CHAIN
<222> LOCATION: 135..244
<223> OTHER INFORMATION: variable light chain

<400> SEQUENCE: 6

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Met Ser Arg Asp Asn Ala Lys Asn Ser Leu Tyr
65                  70                  75                  80

Leu Gln Met Asn Ser Leu Arg Val Glu Asp Ser Ala Val Tyr Tyr Cys
                85                  90                  95

Ala Thr Gly His Tyr Gly Asp Tyr Val Trp Gly Gln Gly Ala Leu Val
            100                 105                 110

Thr Val Ser Ser Gly Ser Ala Ser Ala Pro Lys Leu Glu Glu Gly Glu
        115                 120                 125

Phe Ser Glu Ala Arg Val Gln Ala Gly Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Ser Asn Thr Val Asn Trp Tyr Gln Gln Leu Pro Gly
                165                 170                 175

Thr Ala Pro Lys Leu Leu Ile Tyr Ser Asn Asn Gln Arg Pro Ser Gly
            180                 185                 190

Val Pro Asp Arg Phe Ser Gly Ser Lys Ser Gly Thr Ser Ala Ser Leu
```

Ala Ile Ser Gly Leu Gln Ser Glu Asp Glu Ala Asp Tyr Tyr Cys Ala
         210                 215                 220

Ala Trp Asp Asp Ser Leu Asn Gly Pro Val Phe Gly Gly Gly Thr Lys
225                 230                 235                 240

Leu Thr Val Leu

<210> SEQ ID NO 7
<211> LENGTH: 246
<212> TYPE: PRT
<213> ORGANISM: Artificial Sequence
<220> FEATURE:
<221> NAME/KEY: CHAIN
<222> LOCATION: 1..118
<223> OTHER INFORMATION: variable heavy chain
<220> FEATURE:
<223> OTHER INFORMATION: scFv (SH1319-D4)
<220> FEATURE:
<221> NAME/KEY: CHAIN
<222> LOCATION: 119..136
<223> OTHER INFORMATION: linker
<220> FEATURE:
<221> NAME/KEY: CHAIN
<222> LOCATION: 137..246
<223> OTHER INFORMATION: variable light chain

<400> SEQUENCE: 7

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ser Ser Gly Gly Ala Phe Asp Ile Trp Gly Gln Gly Thr
            100                 105                 110

Val Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Gly Ser Asp Val Gly Gly Tyr Lys Tyr Val Ser Trp Tyr Gln His
                165                 170                 175

His Pro Gly Lys Ala Pro Arg Leu Ile Ile Tyr Asp Val Asn Tyr Trp
            180                 185                 190

Pro Ser Gly Val Ser His Arg Phe Ser Gly Ser Lys Ser Gly Asn Thr
        195                 200                 205

Ala Ser Leu Thr Ile Ser Gly Leu Gln Ser Glu Asp Glu Ala Asp Tyr
    210                 215                 220

Tyr Cys Ser Ser Tyr Arg Thr Gly Asp Thr Trp Val Phe Gly Gly Gly
225                 230                 235                 240

Thr Lys Leu Thr Val Leu
                245

<210> SEQ ID NO 8
<211> LENGTH: 248
<212> TYPE: PRT
<213> ORGANISM: Artificial Sequence
<220> FEATURE:
<221> NAME/KEY: CHAIN
<222> LOCATION: 1..123
<223> OTHER INFORMATION: variable heavy chain
<220> FEATURE:
<223> OTHER INFORMATION: scFv (SH1319-D8)
<220> FEATURE:
<221> NAME/KEY: CHAIN
<222> LOCATION: 124..141
<223> OTHER INFORMATION: linker
<220> FEATURE:
<221> NAME/KEY: CHAIN
<222> LOCATION: 142..248
<223> OTHER INFORMATION: variable light chain

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Phe Ser Trp Val Arg Gln Ala Pro Gly Gln Gly Leu Glu Trp Met
        35                  40                  45

Gly Glu Ile Ile Pro Met Phe Gly Thr Ala Asn Tyr Ala Gln Lys Leu
    50                  55                  60

Gln Gly Arg Val Thr Ile Thr Ala Glu Thr Ser Thr Ser Thr Val Tyr
65                  70                  75                  80

Met Glu Leu Ser Ser Leu Arg Ser Glu Asp Thr Ala Thr Tyr Tyr Cys
                85                  90                  95

Ala Arg Val Pro Arg Ser Ser Gly Tyr Asn Tyr Gly Met Asp Val
            100                 105                 110

Trp Gly Gln Gly Thr Thr Val Thr Val Ser Ser Gly Ser Ala Ser Ala
            115                 120                 125

Pro Lys Leu Glu Glu Gly Glu Phe Ser Glu Ala Arg Val Asp Ile Gln
        130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Gly Ile Ser Asn Tyr Leu Ala Trp
                165                 170                 175

Tyr Gln Gln Lys Pro Gly Lys Val Pro Lys Leu Leu Ile Tyr Ala Ala
            180                 185                 190

Ser Thr Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Val
    210                 215                 220

Ala Thr Tyr Tyr Cys Gln Lys Tyr Asn Ser Ala Pro Arg Thr Phe Gly
225                 230                 235                 240

Gln Gly Thr Lys Val Glu Ile Lys
                245

<210> SEQ ID NO 9
<211> LENGTH: 250
<212> TYPE: PRT
<213> ORGANISM: Artificial Sequence
<220> FEATURE:
<221> NAME/KEY: CHAIN
<222> LOCATION: 1..122

```
<223> OTHER INFORMATION: variable heavy chain
<220> FEATURE:
<223> OTHER INFORMATION: scFv (SH1319-E4)
<220> FEATURE:
<221> NAME/KEY: CHAIN
<222> LOCATION: 123..140
<223> OTHER INFORMATION: linker
<220> FEATURE:
<221> NAME/KEY: CHAIN
<222> LOCATION: 141..250
<223> OTHER INFORMATION: variable light chain

<400> SEQUENCE: 9
```

Gln Val Gln Leu Gln Gln Ser Gly Pro Gly Leu Leu Lys Pro Ser Gln
1               5                   10                  15

Thr Leu Ser Leu Thr Cys Ala Val Ser Gly Asp Ser Val Ser Thr Asn
            20                  25                  30

Ser Gly Ala Trp Ser Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Leu Ser Leu Gln Ser Arg Val Thr Ile Lys Ser Asp Arg Ser Lys Asn
65                  70                  75                  80

Gln Phe Ser Leu Gln Leu Asp Ser Val Thr Pro Glu Asp Thr Ala Ile
                85                  90                  95

Tyr Tyr Cys Ala Arg Glu Asn Trp Asn Ser Gly Gly Phe Asp Tyr Trp
            100                 105                 110

Gly Gln Gly Thr Leu Val Thr Val Pro Ser Gly Ser Ala Ser Ala Pro
        115                 120                 125

Lys Leu Glu Glu Gly Glu Phe Ser Glu Ala Arg Val Gln Pro Val Leu
    130                 135                 140

Thr Gln Ser Ser Ser Ala Ser Gly Ser Pro Gly Gln Ser Val Thr Ile
145                 150                 155                 160

Ser Cys Thr Gly Thr Ser Ser Asp Val Gly Gly Tyr Asn Tyr Val Ser
                165                 170                 175

Trp Tyr Gln Gln His Pro Gly Lys Ala Pro Lys Leu Met Ile Tyr Glu
            180                 185                 190

Val Ser Lys Arg Pro Ser Gly Val Pro Asp Arg Phe Ser Gly Ser Lys
        195                 200                 205

Ser Gly Ser Thr Ala Ser Leu Thr Val Ser Gly Leu Gln Ala Glu Asp
    210                 215                 220

Glu Ala Glu Tyr Tyr Cys Ser Ser Tyr Ala Gly Ser Asn Asn Tyr Val
225                 230                 235                 240

Phe Gly Thr Gly Thr Lys Val Thr Val Leu
                245                 250

```
<210> SEQ ID NO 10
<211> LENGTH: 249
<212> TYPE: PRT
<213> ORGANISM: Artificial Sequence
<220> FEATURE:
<221> NAME/KEY: CHAIN
<222> LOCATION: 1..122
<223> OTHER INFORMATION: variable heavy chain
<220> FEATURE:
<223> OTHER INFORMATION: scFv (SH1319-E12)
<220> FEATURE:
<221> NAME/KEY: CHAIN
<222> LOCATION: 123..140
<223> OTHER INFORMATION: linker
<220> FEATURE:
<221> NAME/KEY: CHAIN
```

<222> LOCATION: 141..249
<223> OTHER INFORMATION: variable light chain

<400> SEQUENCE: 10

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Ser Arg Trp Glu Pro Gly Asp Ala Phe Asp Ile Trp
            100                 105                 110

Gly Gln Gly Thr Met Val Thr Val Ser Ser Gly Ser Ala Ser Ala Pro
        115                 120                 125

Lys Leu Glu Glu Gly Glu Phe Ser Glu Ala Arg Val Gln Pro Val Leu
    130                 135                 140

Thr Gln Ser Ser Ser Val Ser Val Ala Pro Gly Lys Thr Ala Arg Val
145                 150                 155                 160

Thr Cys Gly Gly Asp Asn Ile Gly Gly Lys Ser Val His Trp Tyr Gln
                165                 170                 175

Gln Arg Ala Gly Gln Ala Pro Val Leu Val Ile Ser His Asp Thr Asp
            180                 185                 190

Arg Pro Ser Gly Ile Pro Glu Arg Phe Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ala Val Trp Asp Ala Ser Leu Gly Gly Ser Trp Leu Phe
225                 230                 235                 240

Gly Gly Gly Thr Lys Leu Thr Val Leu
                245

<210> SEQ ID NO 11
<211> LENGTH: 252
<212> TYPE: PRT
<213> ORGANISM: Artificial Sequence
<220> FEATURE:
<221> NAME/KEY: CHAIN
<222> LOCATION: 1..122
<223> OTHER INFORMATION: variable heavy chain
<220> FEATURE:
<223> OTHER INFORMATION: scFv (SH1319-F6)
<220> FEATURE:
<221> NAME/KEY: CHAIN
<222> LOCATION: 123..141
<223> OTHER INFORMATION: linker
<220> FEATURE:
<221> NAME/KEY: CHAIN
<222> LOCATION: 142..252
<223> OTHER INFORMATION: variable light chain

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr

```
                    20                  25                  30
Asp Ile Ser Trp Val Arg Gln Ala Pro Gly Gln Gly Leu Glu Trp Met
                35                  40                  45
Gly Trp Ile Ser Ala Tyr Asn Gly Asn Thr Asn Tyr Ala Gln Lys Leu
            50                  55                  60
Gln Gly Arg Val Thr Met Thr Thr Asp Thr Ser Thr Ser Thr Ala Tyr
 65                  70                  75                  80
Met Glu Leu Arg Arg Leu Arg Ser Asp Thr Ala Val Tyr Tyr Cys
                    85                  90                  95
Ala Arg Gly Gly Arg Trp Leu Arg Ser Ala Ser Ser Phe Asp Tyr Trp
                100                 105                 110
Gly Gln Gly Thr Leu Val Thr Val Ser Ser Gly Ser Ala Ser Ala Pro
                115                 120                 125
Lys Leu Glu Glu Gly Glu Phe Ser Glu Ala Arg Val Gln Ala Gly Leu
            130                 135                 140
Thr Gln Pro Pro Ser Val Ser Gly Ala Pro Gly Gln Arg Val Thr Ile
145                 150                 155                 160
Ser Cys Thr Gly Ser Ser Ser Asn Ile Gly Ala Ala Tyr Asp Val His
                165                 170                 175
Trp Tyr Gln Gln Leu Pro Gly Ala Ala Pro Lys Leu Leu Ile Phe Gly
                180                 185                 190
Asp Ser Asn Arg Pro Ser Gly Val Pro Asp Arg Phe Ser Gly Ser Lys
                195                 200                 205
Ser Asp Thr Ser Ala Ser Leu Ala Ile Thr Gly Leu Gln Ala Glu Asp
            210                 215                 220
Glu Ala Asp Tyr Tyr Cys Gln Ser Phe Asp Ser Ser Leu Ser Gly Ser
225                 230                 235                 240
Arg Val Phe Gly Gly Gly Thr Lys Leu Thr Val Leu
                245                 250

<210> SEQ ID NO 12
<211> LENGTH: 251
<212> TYPE: PRT
<213> ORGANISM: Artificial Sequence
<220> FEATURE:
<221> NAME/KEY: CHAIN
<222> LOCATION: 1..123
<223> OTHER INFORMATION: variable heavy chain
<220> FEATURE:
<223> OTHER INFORMATION: scFv (SH1319-G3)
<220> FEATURE:
<221> NAME/KEY: CHAIN
<222> LOCATION: 124..141
<223> OTHER INFORMATION: linker
<220> FEATURE:
<221> NAME/KEY: CHAIN
<222> LOCATION: 142..251
<223> OTHER INFORMATION: variable light chain

<400> SEQUENCE: 12

Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Asp His
                20                  25                  30
Tyr Met Ser Trp Val Arg Gln Ala Pro Gly Lys Gly Leu Glu Trp Val
                35                  40                  45
Ser Tyr Ile Thr Ser Gly Gly Ser Ser Ile Tyr Tyr Ala Asp Ser Val
            50                  55                  60
Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Gly Leu Asp Ser Ser Ala Tyr Gln Gly Arg Ala Phe Asp Ile
                100                 105                 110

Trp Gly Gln Gly Thr Met Val Thr Val Ser Ser Gly Ser Ala Ser Ala
                115                 120                 125

Pro Lys Leu Glu Glu Gly Glu Phe Ser Glu Ala Arg Val Leu Pro Val
            130                 135                 140

Leu Thr Gln Pro Pro Ser Ala Ser Gly Thr Pro Gly Gln Arg Val Thr
145                 150                 155                 160

Ile Ser Cys Ser Gly Ser Ser Asn Ile Gly Ser Asn Pro Val His
                165                 170                 175

Trp Tyr Gln Gln Leu Pro Gly Thr Ala Pro Lys Leu Leu Val Tyr Arg
                180                 185                 190

Asn Asn Gln Arg Pro Ser Gly Val Pro Asp Arg Phe Ser Gly Ser Lys
                195                 200                 205

Ser Gly Thr Ser Ala Ser Leu Ala Ile Ser Gly Leu Arg Ser Glu Asp
            210                 215                 220

Glu Ala Asp Tyr Tyr Cys Ala Ala Trp Asp Val Ser Leu Ser Gly Val
225                 230                 235                 240

Val Phe Gly Gly Gly Thr Lys Leu Thr Val Leu
                245                 250

<210> SEQ ID NO 13
<211> LENGTH: 81
<212> TYPE: PRT
<213> ORGANISM: Artificial Sequence
<220> FEATURE:
<223> OTHER INFORMATION: CD8 hinge domain and transmembran domain

<400> SEQUENCE: 13

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
                20                  25                  30

Arg Pro Glu Ala Ser Arg Pro Ala Ala Gly Gly Ala Val His Thr Arg
            35                  40                  45

Gly Leu Asp Phe Ala Asp Ile Tyr Ile Trp Ala Pro Leu Ala Gly Thr
        50                  55                  60

Cys Gly Val Leu Leu Leu Ser Leu Val Ile Thr Leu Tyr Cys Asn His
65                  70                  75                  80

Arg

<210> SEQ ID NO 14
<211> LENGTH: 42
<212> TYPE: PRT
<213> ORGANISM: Artificial Sequence
<220> FEATURE:
<223> OTHER INFORMATION: CD28 signalling domain

<400> SEQUENCE: 14

Trp Val Arg Ser Lys Arg Ser Arg Leu Leu His Ser Asp Tyr Met Asn
1               5                   10                  15

Met Thr Pro Arg Arg Pro Gly Pro Thr Arg Lys His Tyr Gln Pro Tyr
                20                  25                  30

Ala Pro Pro Arg Asp Phe Ala Ala Tyr Arg
```

<210> SEQ ID NO 15
<211> LENGTH: 113
<212> TYPE: PRT
<213> ORGANISM: Artificial Sequence
<220> FEATURE:
<223> OTHER INFORMATION: CD3zeta signalling domain

<400> SEQUENCE: 15

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

Ser
```

<210> SEQ ID NO 16
<211> LENGTH: 306
<212> TYPE: PRT
<213> ORGANISM: Artificial Sequence
<220> FEATURE:
<223> OTHER INFORMATION: scFv (C5)

<400> SEQUENCE: 16

```
Ile Lys Glu Glu Lys Leu Thr Met Lys Tyr Leu Leu Pro Thr Ala Ala
1               5                   10                  15

Ala Gly Leu Leu Leu Leu Ala Ala Gln Pro Ala Met Ala Gln Val Gln
            20                  25                  30

Leu Gln Glu Ser Gly Gly Gly Val Ile Gln Pro Gly Arg Ser Leu Arg
        35                  40                  45

Leu Ser Cys Ala Ala Ser Gly Phe Thr Phe Ser Gly His Gly Phe His
    50                  55                  60

Trp Val Arg Gln Ala Pro Gly Lys Gly Leu Glu Trp Val Ala Val Ile
65                  70                  75                  80

Trp Tyr Asp Gly Ser Lys Thr Phe Tyr Ala Asp Ser Val Lys Gly Arg
                85                  90                  95

Phe Thr Ile Ser Arg Asp Asn Ser Arg Asn Thr Val Phe Leu Gln Met
            100                 105                 110

Asn Ser Leu Arg Ala Glu Asp Thr Ala Val Tyr Tyr Cys Ala Arg Asp
        115                 120                 125

Leu Ser Tyr Tyr Ala Met Asp Val Arg Gly Gln Gly Thr Thr Val Thr
    130                 135                 140

Val Ser Ser Gly Ser Ala Ser Ala Pro Lys Leu Glu Glu Gly Glu Phe
145                 150                 155                 160

Ser Glu Ala Arg Val Gln Thr Val Val Thr Gln Glu Pro Ser Leu Thr
                165                 170                 175

Val Ser Pro Gly Gly Thr Val Thr Leu Thr Cys Ala Ser Ser Thr Gly
```

```
                  180                 185                 190
Ala Val Thr Ser Gly Tyr Tyr Pro Asn Trp Phe Gln Gln Lys Pro Gly
                195                 200                 205
Gln Ala Pro Arg Ala Leu Ile Tyr Ser Thr Ser Asn Lys His Ser Trp
            210                 215                 220
Thr Pro Ala Arg Phe Ser Gly Ser Leu Leu Gly Lys Ala Ala Leu
225                 230                 235                 240
Thr Leu Ser Gly Val Arg Pro Glu Asp Glu Ala Glu Tyr Tyr Cys Leu
                245                 250                 255
Leu Tyr Tyr Gly Gly Ala Arg Val Phe Gly Gly Thr Lys Leu Thr
            260                 265                 270
Val Leu Gly Gln Pro Lys Ala Ala Pro Ser Val Thr Leu Phe Pro Pro
            275                 280                 285
Ser Ser Ala Ala Ala Gly Ser Glu Gln Lys Leu Ile Ser Glu Glu Asp
            290                 295                 300
Leu Ser
305

<210> SEQ ID NO 17
<211> LENGTH: 315
<212> TYPE: PRT
<213> ORGANISM: Artificial Sequence
<220> FEATURE:
<223> OTHER INFORMATION: scFv (E4)

<400> SEQUENCE: 17

Ile Lys Glu Glu Lys Leu Thr Met Lys Tyr Leu Leu Pro Thr Ala Ala
1               5                   10                  15
Ala Gly Leu Leu Leu Leu Ala Ala Gln Pro Ala Met Ala Gln Met Gln
            20                  25                  30
Leu Val Gln Ser Gly Ala Glu Val Lys Lys Pro Gly Ser Ser Val Lys
        35                  40                  45
Val Ser Cys Lys Ala Ser Gly Gly Thr Phe Ser Ser Tyr Ala Ile Ser
    50                  55                  60
Trp Val Arg Gln Ala Pro Gly Gln Gly Leu Glu Trp Met Gly Gly Ile
65                  70                  75                  80
Ile Pro Ile Phe Gly Thr Ala Asp Tyr Ala Gln Lys Phe Gln Gly Arg
                85                  90                  95
Val Thr Ile Thr Ala Asp Glu Ser Thr Ser Thr Ala Tyr Met Glu Leu
            100                 105                 110
Ser Ser Leu Arg Ser Glu Asp Thr Ala Val Tyr Tyr Cys Ala Arg Val
        115                 120                 125
Gly Pro Thr Ser Ser Ser Tyr Tyr Tyr Gly Met Asp Val Trp Gly
    130                 135                 140
Gln Gly Thr Thr Val Thr Val Ser Ser Gly Ser Ala Ser Ala Pro Lys
145                 150                 155                 160
Leu Glu Glu Gly Glu Phe Ser Glu Ala Arg Val Gln Ala Val Leu Thr
                165                 170                 175
Gln Pro Pro Ser Val Ser Gly Ala Pro Gly Gln Arg Val Thr Ile Ser
            180                 185                 190
Cys Thr Gly Ser Ser Ser Asn Ile Gly Ala Gly Tyr Asp Val His Trp
        195                 200                 205
Tyr Gln Gln Leu Pro Gly Thr Ala Pro Lys Leu Leu Ile Tyr Gly Asn
    210                 215                 220
Ser Asn Arg Pro Ser Gly Val Pro Asp Arg Phe Ser Gly Ser Lys Phe
```

```
225              230              235              240

Gly Thr Ser Ala Ser Leu Ala Ile Thr Gly Leu Gln Ala Glu Asp Glu
                245                 250                 255

Ala Asp Tyr Tyr Cys Gln Ser Phe Asp Thr Ser Leu Ser Gly Ser Lys
                260                 265                 270

Val Phe Gly Gly Gly Thr Lys Leu Thr Val Leu Gly Gln Pro Lys Ala
                275                 280                 285

Ala Pro Ser Val Thr Leu Phe Pro Pro Ser Ser Ala Ala Gly Ser
                290                 295                 300

Glu Gln Lys Leu Ile Ser Glu Glu Asp Leu Ser
305                 310                 315

<210> SEQ ID NO 18
<211> LENGTH: 307
<212> TYPE: PRT
<213> ORGANISM: Artificial Sequence
<220> FEATURE:
<223> OTHER INFORMATION: scFv (F11)

<400> SEQUENCE: 18

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Gly Gly
                20                  25                  30

Val Val Gln Pro Gly Arg Ser Leu Arg Leu Ser Cys Ala Ala Ser Gly
                35                  40                  45

Phe Thr Phe Ser Ser Tyr Gly Met His Trp Val Arg Gln Ala Pro Gly
50                  55                  60

Lys Gly Leu Glu Trp Val Ala Val Ile Ser Tyr Asp Gly Arg Asn Val
65                  70                  75                  80

His Tyr Ala Asp Ser Val Lys Gly Arg Phe Thr Ile Ser Arg Asp Asn
                85                  90                  95

Ser Lys Asn Thr Leu His Leu Gln Met Asn Ser Leu Arg Pro Glu Asp
                100                 105                 110

Ser Ala Leu Tyr Tyr Cys Val Lys Asp Leu Ala Arg Val Val Ile Thr
                115                 120                 125

Pro Gly Gly Met His Val Trp Gly Gln Gly Thr Thr Val Thr Val Ser
                130                 135                 140

Ser Gly Ser Ala Phe Ala Pro Lys Leu Glu Glu Gly Glu Phe Ser Glu
145                 150                 155                 160

Ala Arg Val Gln Ala Val Val Thr Gln Glu Pro Ser Leu Ser Val Ser
                165                 170                 175

Pro Gly Gly Thr Val Thr Leu Thr Cys Ala Ser Ser Thr Gly Thr Val
                180                 185                 190

Thr Gly Ala Ser Ser Pro Asn Trp Phe Gln Gln Lys Pro Gly Gln Val
                195                 200                 205

Pro Arg Pro Leu Ile Tyr Gly Thr Thr Asn Lys His Ser Trp Thr Pro
                210                 215                 220

Ala Arg Phe Ser Gly Ser Leu Leu Gly Gly Lys Ala Ala Leu Thr Val
225                 230                 235                 240

Ser Gly Val Gln Pro Glu Asp Glu Ala Glu Tyr Tyr Cys Leu Leu Tyr
                245                 250                 255

Ser Gly Gly Gly Gln Pro Tyr Trp Met Phe Gly Gly Gly Thr Lys Leu
                260                 265                 270

Thr Val Leu Gly Gln Pro Lys Ala Ala Pro Ser Val Thr Leu Phe Pro
```

```
                 275                 280                 285

Pro Ser Ser Ala Ala Gly Ser Glu Gln Lys Leu Ile Ser Glu Glu
        290                 295                 300

Asp Leu Ser
305

<210> SEQ ID NO 19
<211> LENGTH: 310
<212> TYPE: PRT
<213> ORGANISM: Artificial Sequence
<220> FEATURE:
<223> OTHER INFORMATION: scFv (H7)

<400> SEQUENCE: 19

Lys Glu Glu Lys Leu Thr Met Lys Tyr Leu Pro Thr Ala Ala Ala
1               5                   10                  15

Gly Leu Leu Leu Leu Ala Ala Gln Pro Ala Met Ala Gln Val Gln Leu
            20                  25                  30

Val Gln Ser Gly Gly Gly Val Val Gln Pro Gly Arg Ser Leu Arg Leu
            35                  40                  45

Ser Cys Ala Ala Ser Gly Phe Thr Phe Ser Ser Tyr Gly Met His Trp
    50                  55                  60

Val Arg Gln Ala Pro Gly Lys Gly Leu Glu Trp Val Ala Val Ile Ser
65                  70                  75                  80

Tyr Asp Gly Ser Asn Lys Tyr Tyr Ala Asp Ser Val Lys Gly Arg Phe
                85                  90                  95

Thr Ile Ser Arg Asp Asn Ser Lys Asn Thr Leu Tyr Leu Gln Met Asn
            100                 105                 110

Ser Leu Arg Ala Glu Asp Thr Ala Val Tyr Tyr Cys Ala Lys Glu Ala
            115                 120                 125

Tyr Asn Trp Asn Asp Gly Gly Trp Phe Asp Pro Trp Gly Gln Gly Thr
        130                 135                 140

Leu Val Thr Val Ser Ser Gly Ser Ala Ser Ala Pro Lys Leu Glu Glu
145                 150                 155                 160

Gly Glu Phe Ser Glu Ala Arg Val Gln Ala Val Leu Thr Gln Pro Pro
                165                 170                 175

Ser Thr Ser Gly Thr Pro Gly Gln Val Thr Ile Ser Cys Ser Gly
            180                 185                 190

Ser Arg Ser Asn Ile Gly Pro Asn Tyr Val His Trp Tyr Gln Gln Leu
        195                 200                 205

Pro Gly Ala Ala Pro Lys Val Leu Ile Tyr Arg Asn Tyr Gln Arg Pro
    210                 215                 220

Ser Gly Val Pro Asp Arg Ile Ser Ala Ser Lys Ser Gly Thr Ser Ala
225                 230                 235                 240

Ser Leu Ala Ile Ser Gly Leu Arg Ser Glu Asp Glu Ala Val Tyr Tyr
                245                 250                 255

Cys Ala Ser Trp Asp Asp Thr Leu Gly Ala Val Val Phe Gly Gly Gly
            260                 265                 270

Thr Lys Leu Thr Val Leu Gly Gln Pro Lys Ala Ala Pro Ser Val Thr
        275                 280                 285

Leu Phe Pro Pro Ser Ser Ala Ala Gly Ser Glu Gln Lys Leu Ile
    290                 295                 300

Ser Glu Glu Asp Leu Ser
305                 310
```

```
<210> SEQ ID NO 20
<211> LENGTH: 280
<212> TYPE: PRT
<213> ORGANISM: Artificial Sequence
<220> FEATURE:
<223> OTHER INFORMATION: hAFC IgG domain

<400> SEQUENCE: 20

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Arg Gly Ile Leu
        275                 280

<210> SEQ ID NO 21
<211> LENGTH: 184
<212> TYPE: PRT
<213> ORGANISM: Artificial Sequence
<220> FEATURE:
<223> OTHER INFORMATION: hCD28 transmembrane domain - hCD3zeta
      signalling domain

<400> SEQUENCE: 21

Asp Pro Lys Phe Trp Val Leu Val Val Gly Gly Val Leu Ala Cys
1               5                   10                  15

Tyr Ser Leu Leu Val Thr Val Ala Phe Ile Ile Phe Trp Val Arg Ser
                20                  25                  30
```

Lys Arg Ser Arg Leu Leu His Ser Asp Tyr Met Asn Met Thr Pro Arg
            35                  40                  45

Arg Pro Gly Pro Thr Arg Lys His Tyr Gln Ala Tyr Ala Ala Ala Arg
 50                  55                  60

Asp Phe Ala Ala Tyr Arg Ser Leu Arg Val Lys Phe Ser Arg Ser Ala
 65                  70                  75                  80

Asp Ala Pro Ala Tyr Gln Gln Gly Gln Asn Gln Leu Tyr Asn Glu Leu
                 85                  90                  95

Asn Leu Gly Arg Arg Glu Glu Tyr Asp Val Leu Asp Lys Arg Arg Gly
            100                 105                 110

Arg Asp Pro Glu Met Gly Gly Lys Pro Arg Arg Lys Asn Pro Gln Glu
            115                 120                 125

Gly Leu Tyr Asn Glu Leu Gln Lys Asp Lys Met Ala Glu Ala Tyr Ser
130                 135                 140

Glu Ile Gly Met Lys Gly Glu Arg Arg Arg Gly Lys Gly His Asp Gly
145                 150                 155                 160

Leu Tyr Gln Gly Leu Ser Thr Ala Thr Lys Asp Thr Tyr Asp Ala Leu
                165                 170                 175

His Met Gln Ala Leu Pro Pro Arg
            180

<210> SEQ ID NO 22
<211> LENGTH: 452
<212> TYPE: PRT
<213> ORGANISM: Artificial Sequence
<220> FEATURE:
<223> OTHER INFORMATION: fusion P2A hFOXP3

<400> SEQUENCE: 22

Gly Ala Thr Asn Phe Ser Leu Leu Lys Gln Ala Gly Asp Val Glu Glu
 1               5                  10                  15

Asn Pro Gly Pro Ser Met Pro Asn Pro Arg Pro Gly Lys Pro Ser Ala
             20                  25                  30

Pro Ser Leu Ala Leu Gly Pro Ser Pro Gly Ala Ser Pro Ser Trp Arg
            35                  40                  45

Ala Ala Pro Lys Ala Ser Asp Leu Leu Gly Ala Arg Gly Pro Gly Gly
 50                  55                  60

Thr Phe Gln Gly Arg Asp Leu Arg Gly Gly Ala His Ala Ser Ser Ser
 65                  70                  75                  80

Ser Leu Asn Pro Met Pro Pro Ser Gln Leu Gln Leu Pro Thr Leu Pro
                 85                  90                  95

Leu Val Met Val Ala Pro Ser Gly Ala Arg Leu Gly Pro Leu Pro His
            100                 105                 110

Leu Gln Ala Leu Leu Gln Asp Arg Pro His Phe Met His Gln Leu Ser
            115                 120                 125

Thr Val Asp Ala His Ala Arg Thr Pro Val Leu Gln Val His Pro Leu
130                 135                 140

Glu Ser Pro Ala Met Ile Ser Leu Thr Pro Pro Thr Thr Ala Thr Gly
145                 150                 155                 160

Val Phe Ser Leu Lys Ala Arg Pro Gly Leu Pro Pro Gly Ile Asn Val
                165                 170                 175

Ala Ser Leu Glu Trp Val Ser Arg Glu Pro Ala Leu Leu Cys Thr Phe
            180                 185                 190

Pro Asn Pro Ser Ala Pro Arg Lys Asp Ser Thr Leu Ser Ala Val Pro
            195                 200                 205

Gln Ser Ser Tyr Pro Leu Leu Ala Asn Gly Val Cys Lys Trp Pro Gly
    210                 215                 220

Cys Glu Lys Val Phe Glu Pro Glu Asp Phe Leu Lys His Cys Gln
225                 230                 235                 240

Ala Asp His Leu Leu Asp Glu Lys Gly Arg Ala Gln Cys Leu Leu Gln
            245                 250                 255

Arg Glu Met Val Gln Ser Leu Glu Gln Gln Leu Val Leu Glu Lys Glu
        260                 265                 270

Lys Leu Ser Ala Met Gln Ala His Leu Ala Gly Lys Met Ala Leu Thr
    275                 280                 285

Lys Ala Ser Ser Val Ala Ser Ser Asp Lys Gly Ser Cys Cys Ile Val
290                 295                 300

Ala Ala Gly Ser Gln Gly Pro Val Val Pro Ala Trp Ser Gly Pro Arg
305                 310                 315                 320

Glu Ala Pro Asp Ser Leu Phe Ala Val Arg Arg His Leu Trp Gly Ser
            325                 330                 335

His Gly Asn Ser Thr Phe Pro Glu Phe Leu His Asn Met Asp Tyr Phe
        340                 345                 350

Lys Phe His Asn Met Arg Pro Pro Phe Thr Tyr Ala Thr Leu Ile Arg
    355                 360                 365

Trp Ala Ile Leu Glu Ala Pro Glu Lys Gln Arg Thr Leu Asn Glu Ile
370                 375                 380

Tyr His Trp Phe Thr Arg Met Phe Ala Phe Phe Arg Asn His Pro Ala
385                 390                 395                 400

Thr Trp Lys Asn Ala Ile Arg His Asn Leu Ser Leu His Lys Cys Phe
            405                 410                 415

Val Arg Val Glu Ser Glu Lys Gly Ala Val Trp Thr Val Asp Glu Leu
        420                 425                 430

Glu Phe Arg Lys Lys Arg Ser Gln Arg Pro Ser Arg Cys Ser Asn Pro
    435                 440                 445

Thr Pro Gly Pro
    450

<210> SEQ ID NO 23
<211> LENGTH: 280
<212> TYPE: PRT
<213> ORGANISM: Artificial Sequence
<220> FEATURE:
<223> OTHER INFORMATION: ΔLNGFR (reporter)

<400> SEQUENCE: 23

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
            85                  90                  95

Ala Pro Cys Val Glu Ala Asp Asp Ala Val Cys Arg Cys Ala Tyr Gly
        100                 105                 110

```
Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
        130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
        210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
                260                 265                 270

Lys Arg Trp Asn Arg Gly Ile Leu
            275                 280

<210> SEQ ID NO 24
<211> LENGTH: 21
<212> TYPE: PRT
<213> ORGANISM: Artificial Sequence
<220> FEATURE:
<223> OTHER INFORMATION: secretory leader peptide

<400> SEQUENCE: 24

Met Ala Leu Pro Val Thr Ala Leu Leu Leu Pro Leu Ala Leu Leu Leu
1               5                   10                  15

His Ala Ala Ala Pro
            20

<210> SEQ ID NO 25
<211> LENGTH: 25
<212> TYPE: PRT
<213> ORGANISM: Artificial Sequence
<220> FEATURE:
<223> OTHER INFORMATION: secretory leader peptide

<400> SEQUENCE: 25

Met Asp Phe Gln Val Gln Ile Phe Ser Phe Leu Leu Ile Ser Ala Ser
1               5                   10                  15

Val Ile Met Ser Arg Gly Val His Ser
            20                  25
```

FUSION PROTEIN FOR USE IN THE TREATMENT OF HVG DISEASE

The present invention relates to a fusion protein for use in the treatment of HvG disease in a patient having received a transplant, for use in suppressing the host's immune response directed against the transplant. The fusion protein is adapted for use in suppressing the immune rejection of a transplant which contains or expresses an MHC class I molecule, which is the human HLA-A*02 in a recipient patient who is negative for HLA-A*02, i.e. the patient prior to transplantation does not express HLA-A*02, or the fusion protein is adapted for use in suppressing the immune reaction of a transplant which contains or expresses an MHC class I molecule, which is the porcine SLA-01*0401 (swine leucocyte antigen 01*0401). The fusion protein is a chimeric antigen receptor (CAR-A*02 or CAR-SLA-01*0401), which upon expression in regulatory T-cells ($T_{reg}$) causes a specific suppressor activity of the regulatory T-cells in the presence of HLA-A*02 or in the presence of SLA-01*0401, respectively. It is an advantage of the CAR-A*02 and CAR-SLA-01*0401 of the invention that the suppressor activity is limited to the transplant and results in the suppression of cytotoxic T-cells within the transplant, including cytotoxic T-cells directed against the transplant expressing HLA-A*02 or SLA-01*0401, respectively. The transplant is a solid tissue.

The fusion protein comprises or consists of a single-chain variable fragment antibody domain (scFv), a modified hCD8 hinge, a hCD8 transmembrane domain, an intracellular hCD28 signalling domain and an intracellular hCD3ζ (hCD3 zeta) signalling domain, which preferably are linked to one another from N-terminus to C-terminus, more preferably directly linked to one another form N-terminus to C-terminus.

The fusion protein can, especially in the CAR-SLA-01*0401, contain a hΔFc IgG domain in the alternative to a modified hCD8 hinge, and/or a fusion hCD28 transmembrane domain—hCD28/CD3 zeta domain in the alternative to a hCD8 transmembrane domain, an intracellular hCD28 signalling domain and an intracellular hCD3ζ (hCD3 zeta) signalling domain.

Further, the invention relates to a nucleic acid sequence encoding the CAR fusion protein, preferably contained in a viral vector, e.g. between a 5'R and a 3'R, the nucleic acid sequence more preferably being contained in a viral particle suitable for transducing Treg cells. Therein, the nucleic acid sequence and a viral vector, preferably contained in a viral particle, are for use in the treatment of Host-versus-Graft (HvG) disease. According to the invention, the treatment of HvG disease generally is the suppression of cytotoxic T-cell activity directed against the transplanted graft.

Further, the invention relates to an in vitro method for introducing suppressor activity specific for HLA-A*02 or SLA-01*0401, respectively, by expressing the fusion protein according to the invention in Treg cells, e.g. by introducing a nucleic acid sequence encoding the fusion protein CAR-A*02 or CAR-SLA-01*0401 into Treg cells, which Treg cells generally do not contain or express HLA-A*02 nor SLA-01*0401, and preferably the Treg cells are homogeneic to the patient, e.g. obtained and isolated from a biopsy of the patient. The invention provides a method of treatment of HvG disease, comprising the administration of Treg cells expressing the fusion protein CAR-A*02 or the fusion protein CAR-SLA-01*0401 according to the invention to the patient.

PRIOR ART

MacDonald et al., The Journal of Clinical Investigation 1-12 (22 Mar. 2016) describes a generic CAR having an scFv domain specific for HLA-A2, and regulatory T-cells transduced for expressing the CAR for HLA-A2-specific suppression. The scFv domain contained the heavy and light chain variable regions of the monoclonal antibody BB7.2. In addition to the scFv, the CAR contained a CD28 transmembrane domain, a CD28 signalling domain and a CD3ζ signalling domain.

Inaguma et al., Gene Therapy 575-584 (2014) describe the construction of a T-cell receptor useful for directing T-lymphocytes against tumour cells that express a specific protein, comprising isolation of an antibody scFv having specificity for the tumour-specific protein when bound in a HLA-A2 complex, and using the scFv as a domain in the synthetic T-cell receptor.

Noyan et al., Cancer Gene Therapy 19, 352-357 (2012) describe induced transgene expression in hematopoietic stem and progenitor cells by lentiviral transduction for use in the treatment of solid tumours.

Galla et al., Nuc. Ac. Res. 39, 1721-1731 (2009) describe the cytotoxic effects of transposase used in transduction of cells by retroviral particles.

DiStasi et al., N Engl J Med 1673-1683 (2011) describe the genetic manipulation by introduction of sequences encoding caspase-9 dimerizer to generate a system for inducible apoptosis in the cells.

Long et al., Diabetes, 407-415 (2010) describe an assay for measuring STAT5 phosphorylation in the signalling pathway of IL-2R.

Hombach et al., Gene Therapy 1206-1213 (2010) describe a CAR for use in directing T-cells against a specific antigen, the CAR containing a modified IgG1 Fc spacer domain between an scFv and the transmembrane domain, to which transmembrane domain a signalling domain (CD28-CD3ζ) is attached.

OBJECT OF THE INVENTION

The object of the invention is the provision of a chimeric antigen receptor CAR suitable for providing Treg cells with suppressor activity for an MHC class I, especially for HLA-A*02 or for CAR-SLA-01*0401, sufficiently strong to suppress the cytotoxic rejection of a transplant expressing the MHC class I, e.g. HLA-A*02 or SLA-01*0401, especially in a recipient patient who is HLA-A*02 negative, for use in the treatment of HvG disease.

DESCRIPTION OF THE INVENTION

The invention achieves the object by the features of the claims, especially by providing a fusion protein which is chimeric antigen receptor (CAR), especially CAR-A*02 which contains an scFv domain that is specific for the human HLA-A*02 or CAR-SLA-01*0401 which contains a scFv domain that is specific for the porcine SLA-01*0401, which CAR-A*02 or CAR-SLA-01*0401 is for use in the treatment of HvG disease, e.g. for use in the treatment of cytotoxic rejection reactions in transplant recipient patients. The CAR-A*02 provides for suppression of cytotoxic T-cells when the CAR-A*02 is expressed in human Treg cells in the presence of the human HLA-A*02. The CAR-A*02, when expressed in a human Treg cell, and respectively the human Treg cell expressing the CAR-A*02, is a pharmaceutical compound for the treatment of HvG disease.

Correspondingly, the CAR-SLA-01*0401 when expressed in human Treg cells, and respectively the human Treg cell expressing the CAR-SLA-01*0401 is a pharmaceutical compound for the treatment of HvG disease, when the transplanted tissue is of porcine origin and expresses SLA-01*0401. The CAR-SLA-01*0401 upon expression in a Treg cell of the transplant recipient has the advantage of suppressing the HvG directed against a transplant of porcine origin. A transplant of porcine origin can e.g. be pancreatic tissue, preferably islets.

Optionally, a Treg cell expressing the CAR-A*02 or CAR-SLA-01*0401 is genetically manipulated to also express FOXP3, preferably constitutively, e.g. by introduction of an expression cassette encoding human FOXP3 concurrent with introducing the nucleic acid sequence encoding the CAR-A*02 into a Treg cell. Further optionally, in addition to or in the alternative to genetic manipulation of a Treg cell to express FOXP3, a Treg cell in addition to expressing the CAR-A*02 or CAR-SLA-01*0401 can be genetically manipulated to express a caspase-9 dimerizer system (e.g. as described by DiStasi et al., N Engl J Med 1673-1683 (2011)) for depletion of the Treg cells following transfer into a patient.

Expression of FOXP3 with the fusion protein CAR-A*02 or CAR-SLA-01*0401, respectively, can be by expression of a fusion of P2A with C-terminally fused FOXP3 in one unified fusion protein, e.g. directly fused to the C-terminus of CAR-A*02 or CAR-SLA-01*0401, respectively. Such a fusion, e.g. encoded by one expression cassette adapted to generate one unified mRNA encoding the fusion protein of CAR-P2A-FOXP3, would yield free FOXP3 by its hydrolysis from the P2A domain. An exemplary fusion of P2A-FOXP3 is SEQ ID NO: 22, which can directly be fused to the C-Terminus of the hCD3ζ domain of the fusion protein.

The CAR-A*02 or CAR-SLA-01*0401, respectively, is a fusion protein comprising or consisting of a single-chain variable fragment antibody domain (scFv), a hinge, a transmembrane domain, an intracellular hCD28 signalling domain and an intracellular CD3 signalling domain, also termed hCD3ζ (hCD3 zeta) domain, which domains preferably are linked directly to one another from N-terminus to C-terminus. In the scFv domain, a variable light chain of an antibody is connected by a hinge region to a variable heavy chain of an antibody. The CAR-A*02 is characterized by its scFv domain being selected from the amino acid sequences of one of SEQ ID NO: 1 to SEQ ID NO: 12, the CD8 hinge and CD8 transmembrane domain preferably has an amino acid sequence of SEQ ID NO: 13, the CD28 signalling domain preferably has an amino acid sequence of SEQ ID NO: 14, and the CD3 signalling domain has an amino acid sequence of SEQ ID NO: 15. The CAR-SLA-01*0401 is characterized by its scFv domain being selected from the amino acid sequences of one of SEQ ID NO: 16 to SEQ ID NO: 19. As the signalling domains according to the invention have a human or humanized amino acid sequence, this is herein also indicated by a "h". The hinge and can be formed by the hΔFc IgG domain, preferably of SEQ ID NO: 20. The CD8 transmembrane domain, hCD28 signalling domain and hCD3ζ signalling domain can be exchanged for a fusion of a hCD28 transmembrane domain, hCD28 signalling domain and the hCD3ζ signalling domain, preferably of SEQ ID NO: 21.

The CAR-A*02 fusion protein has the advantage that it is highly specific for the HLA-A*02. The CAR-SLA-01*0401 fusion protein has the advantage that it is highly specific for the SLA-01*0401. Its expression in Tregs leads to an enhancement of Treg proliferation in the presence of HLA-A*02 or SLA-01*0401, respectively, and results in increased Teff (effector T-cell) suppressor activity.

The fusion protein CAR-A*02 or CAR-SLA-01*0401 can be expressed in a Treg from a nucleic acid sequence encoding the fusion protein in an expression cassette. Optionally, the expression cassette encoding the fusion protein CAR-A*02 or CAR-SLA-01*0401 is contained in a viral vector for introduction of the nucleic acid sequence, e.g. by transduction using a viral particle containing the viral vector.

For in vitro production of Treg cells expressing the CAR-A*02, Treg cells originating from the recipient of the transplant, who can be a future recipient or a recipient having received a transplant, are used preferably. Treg cells are CD4+, CD25high and CD127low and have to be isolated from HLA-A*02 negative patients, e.g. from a blood sample by cell sorting, e.g. using FACS or magnetic beads with specific antibodies. For in vitro production of Treg cells expressing the CAR-SLA-01*0401, Treg cells originating from the recipient of the transplant, who can be a future recipient or a recipient having received a transplant, are used preferably. Treg cells are CD4+, CD25high and CD127low and have to be isolated e.g. from a blood sample by cell sorting, e.g. using FACS or magnetic beads with specific antibodies It is an advantage of the Treg cells expressing the CAR-A*02 or CAR-SLA-01*0401 that prior to introduction into the patient and respectively following the introduction of the nucleic acid sequence encoding the CAR-A*02 or the CAR-SLA-01*0401, no in vitro expansion is necessary prior to introducing these Treg cells into a patient. For example, no in vitro expansion comprising cultivation of these Treg cells in the presence of stimulating agents in the cultivation medium is carried out in the process for producing these Treg cells. Preferably, following introduction of the nucleic acid sequence encoding the CAR-A*02 or CAR-SLA-01*0401, the Treg cells are kept in culture for about 24 h to allow expression of the CAR-A*02 or CAR-SLA-01*0401, followed by cell sorting to isolate Treg cells expressing the CAR-A*02 or CAR-SLA-01*0401. In this culture, no stimulating agents for expansion are present in the culture medium, e.g. no anti-CD3 or anti-CD28 antibodies. In this culture, the culture medium contains low dose IL-2, e.g. at 50 U/mL medium, in order to keep the Treg cells from dying. It has been found that Treg cells expressing the CAR-A*02 or the CAR-SLA-01*0401 are effective in migrating to the transplant and effective in suppressing a cytotoxic response directed against the transplant and that the Treg cells expressing the CAR-A*02 or respectively CAR-SLA-01*0401 have a stable suppression activity.

The scFv domain of the CAR-A*02 is very specific for the HLA-A*02, and to-date, no cross-reactivity or off-toxicity was found. Further, no intrinsic activity or self-activation of the CAR-A*02 was found, excluding a suppressive activity independent from the presence of HLA-A*02. The suppressive activity of Treg cells expressing the CAR-A*02 was found to be drastically higher than the suppressive activity of naïve Treg (nTreg) cells.

The CAR-A*02, or respectively CAR-SLA-01*0401, can be used in a process for producing Treg cells having suppressive activity in the presence of HLA-A*02 or respectively SLA-01*0401 by introducing a coding sequence for CAR-A*02 or respectively CAR-SLA-01*0401 into Treg cells originating from the donor prior to contact of the donor with HLA-A*02 or respectively SLA-01*0401, or into Treg cells originating from the donor following contact of the donor to HLA-A*02 or respectively SLA-01*0401, e.g. from the recipient of the transplant following transplantation.

Generally preferred, the fusion protein at its N-terminus comprises a leader peptide for secretion of the fusion protein to facilitate transmembrane transport of the scFv domains and arrangement of the transmembrane (TM) domain across the cell membrane. An exemplary leader sequence is SEQ ID NO: 24, preferred for the CAR-A*02, or SEQ ID NO: 25, preferred for the CAR-SLA-01*0401.

Figure 1C:
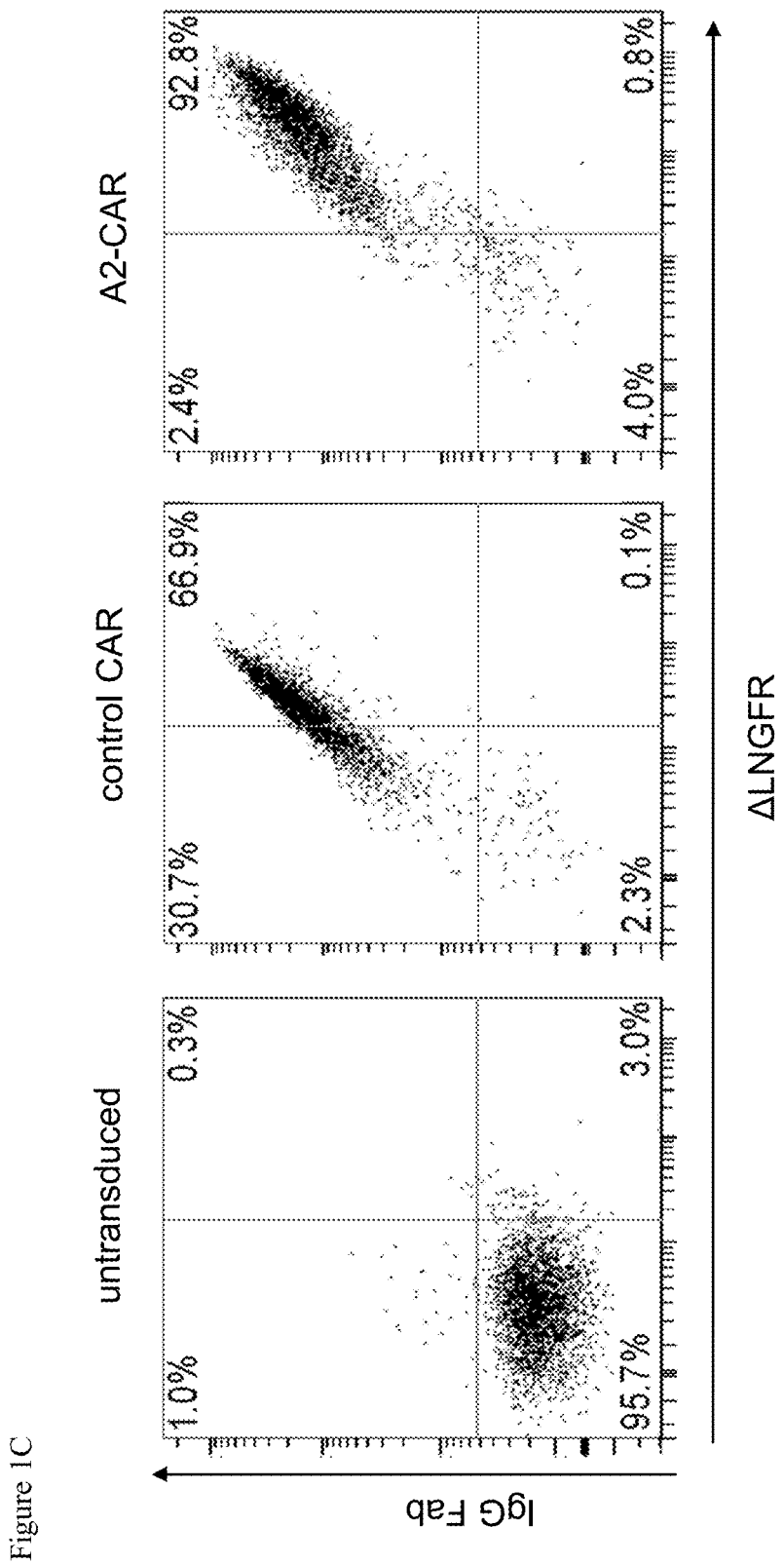
Figure 1D:
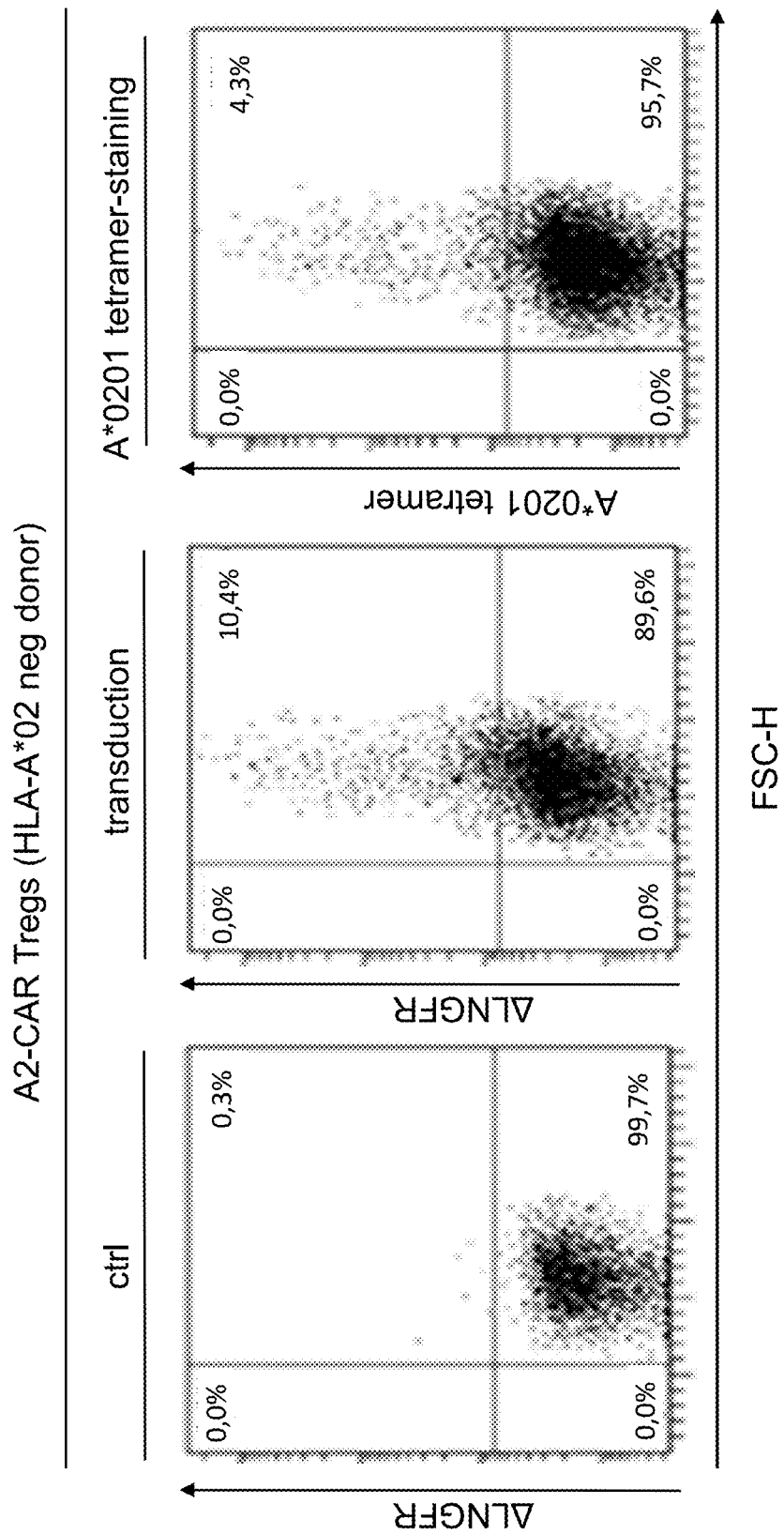
Figures 1, 1E:
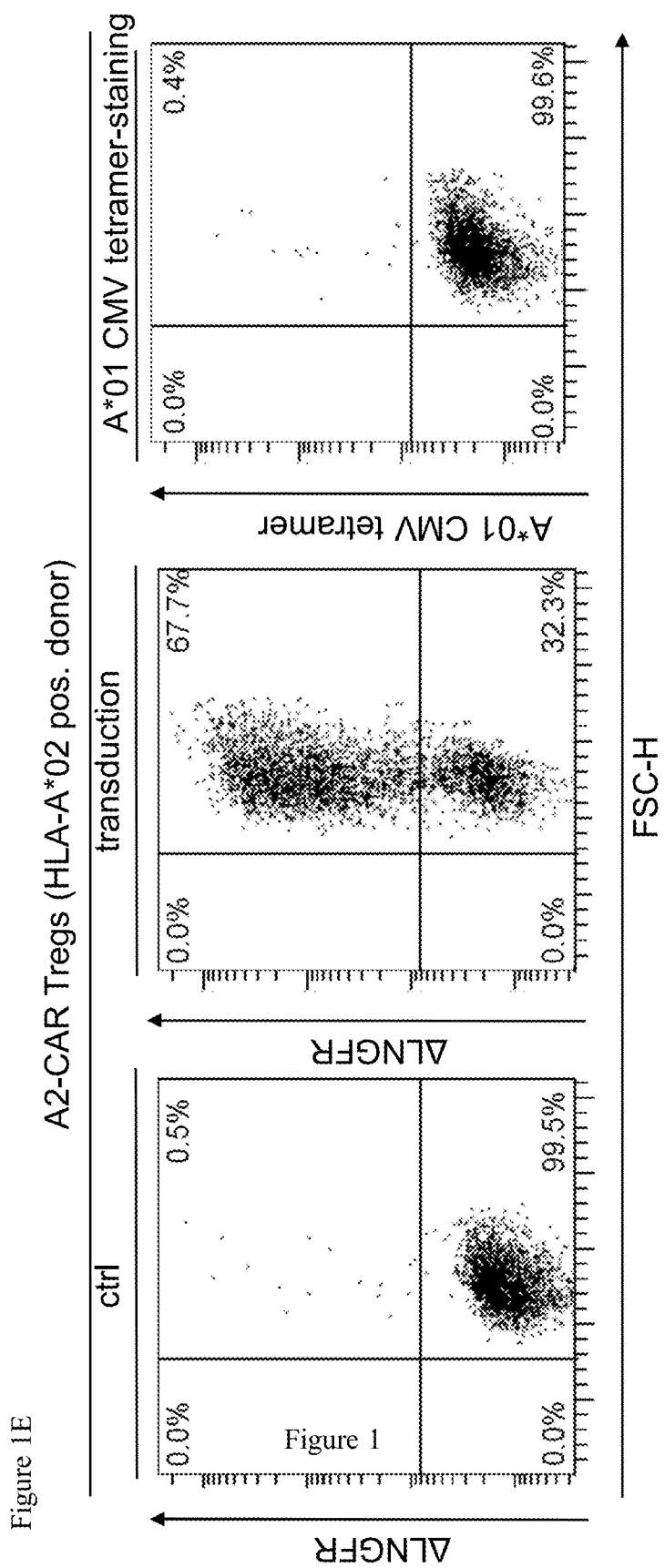
Figure 1F:
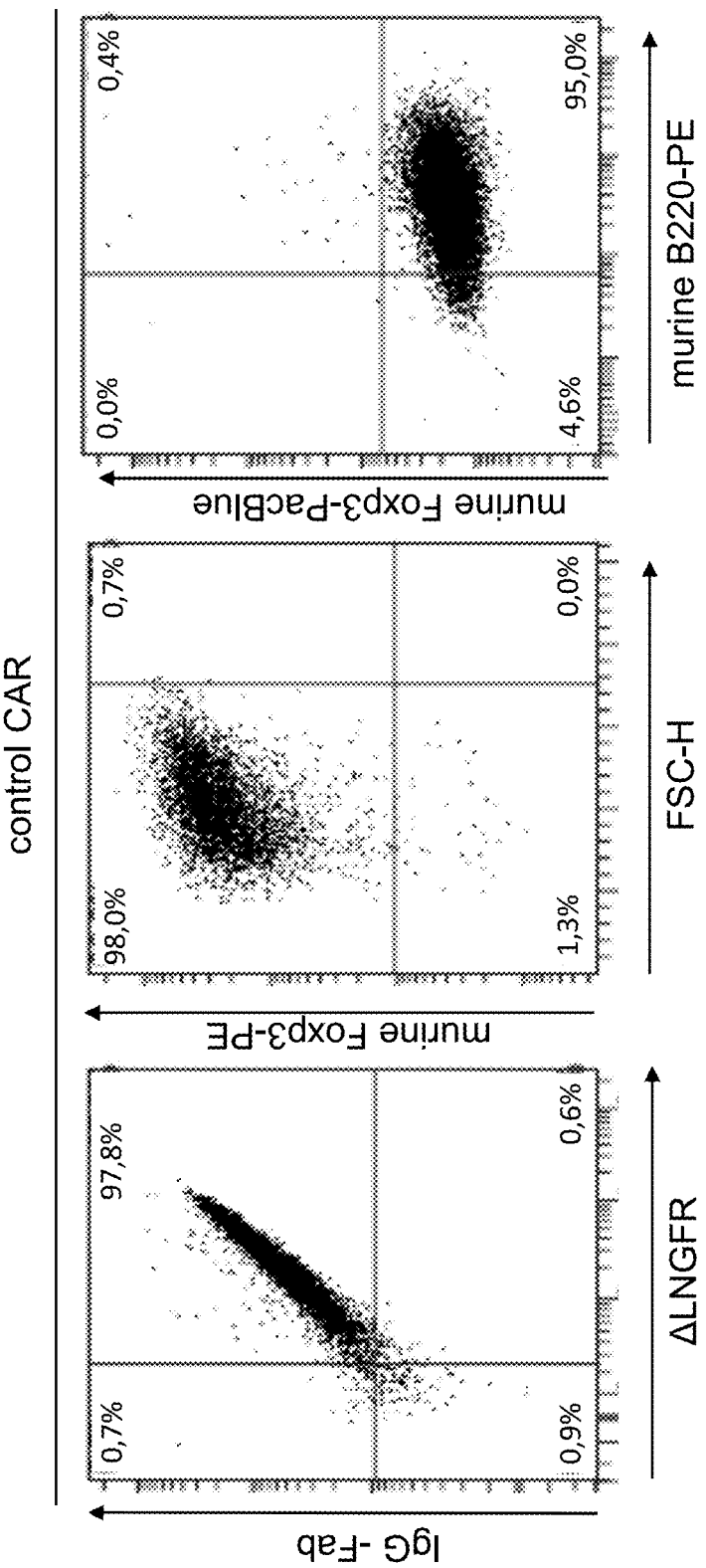
Figure 2A:
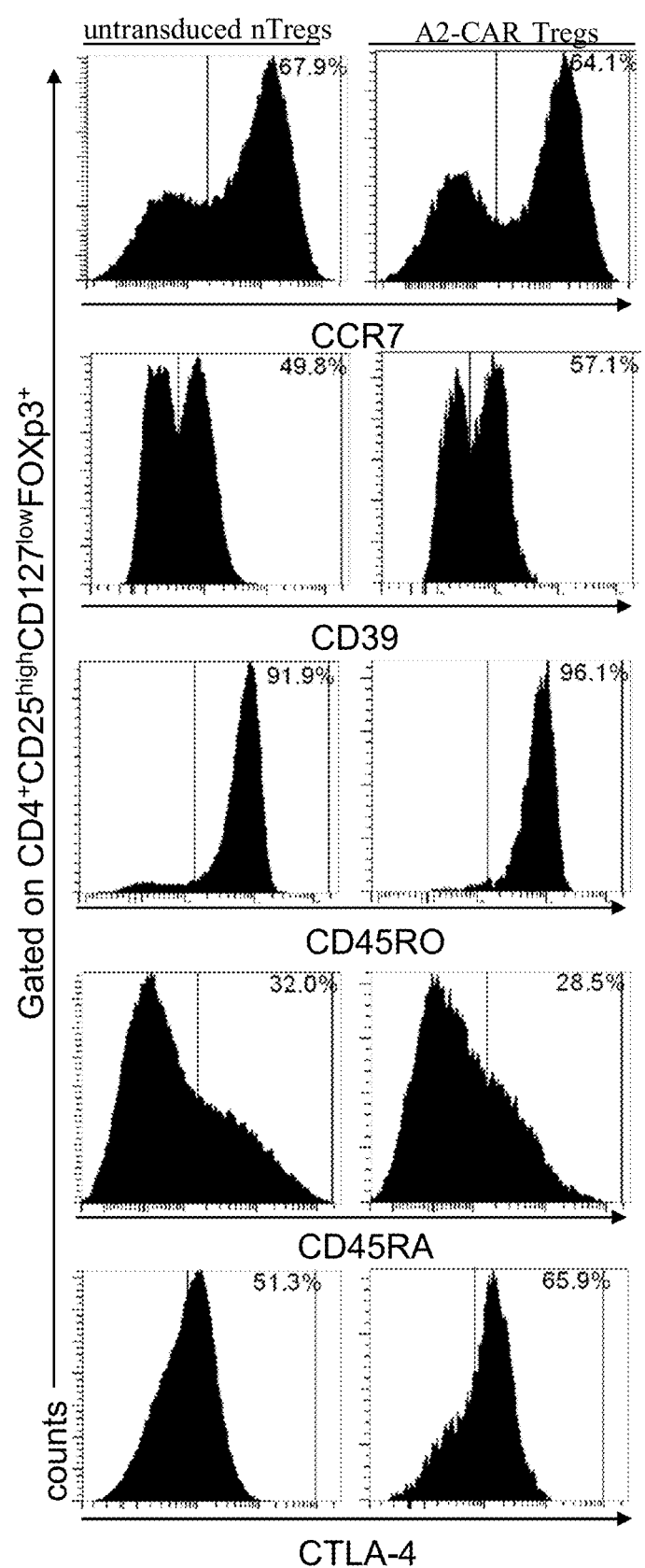
Figure 2B:
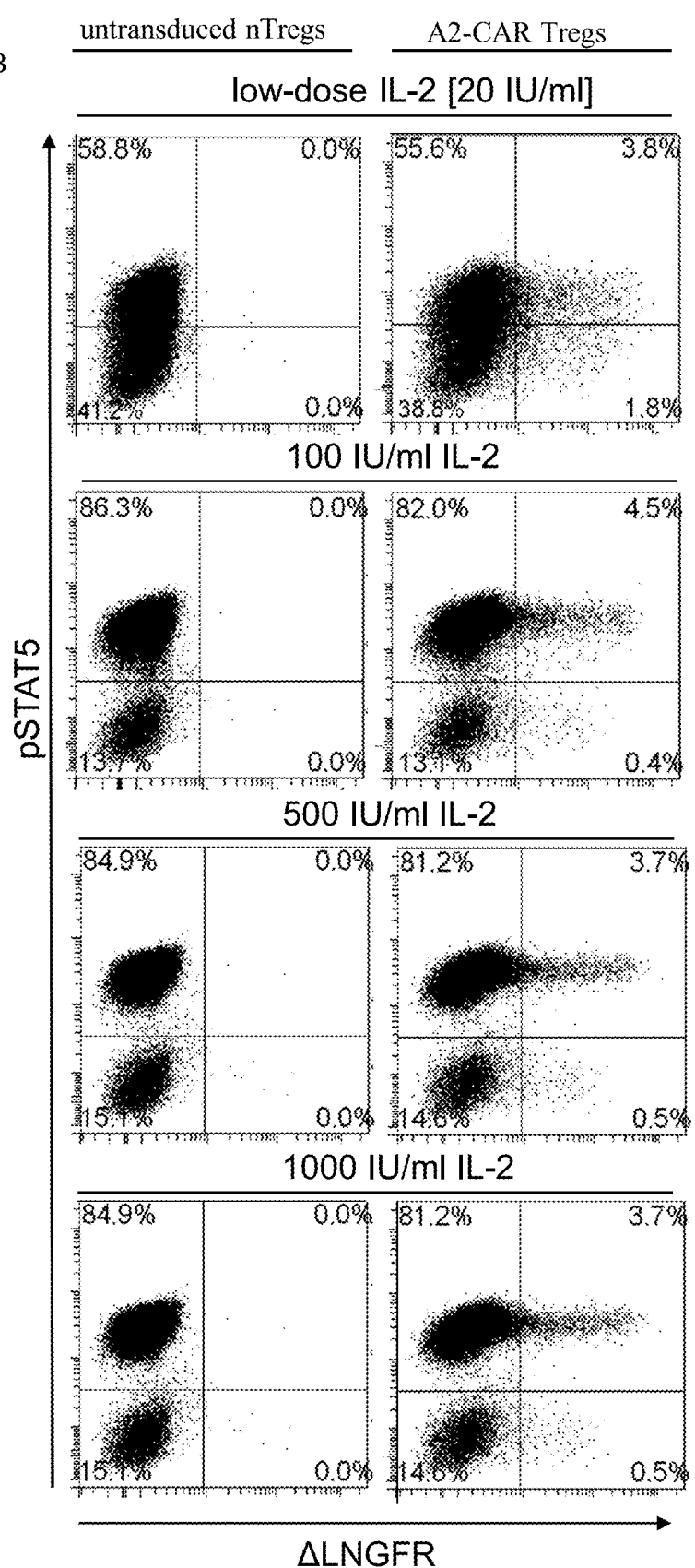
Figure 2C:
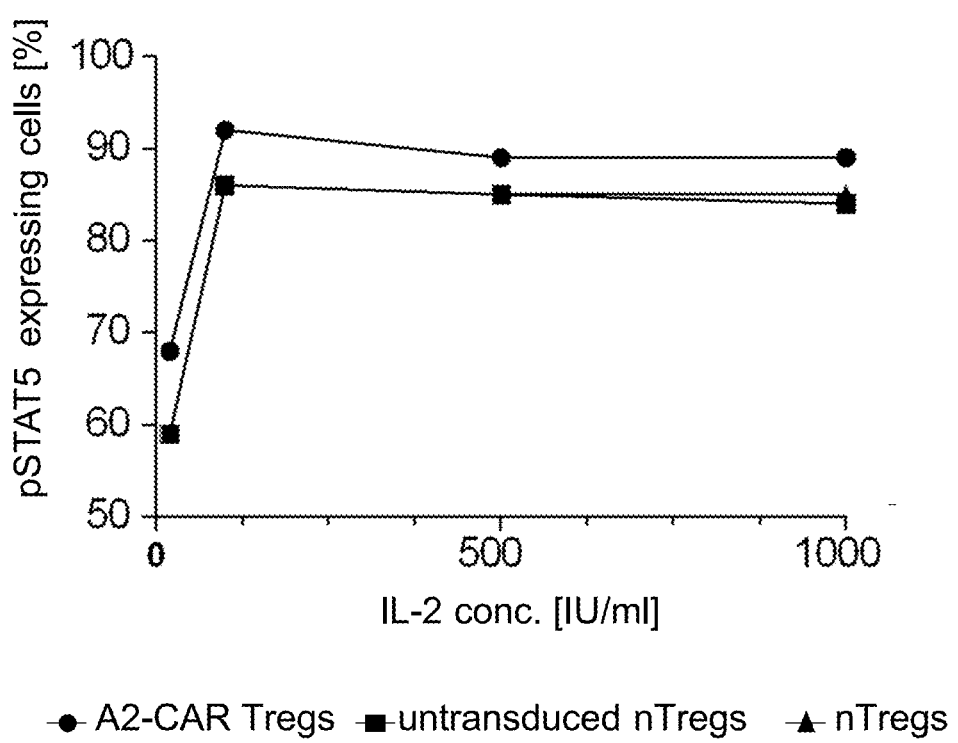
Figure 3B:
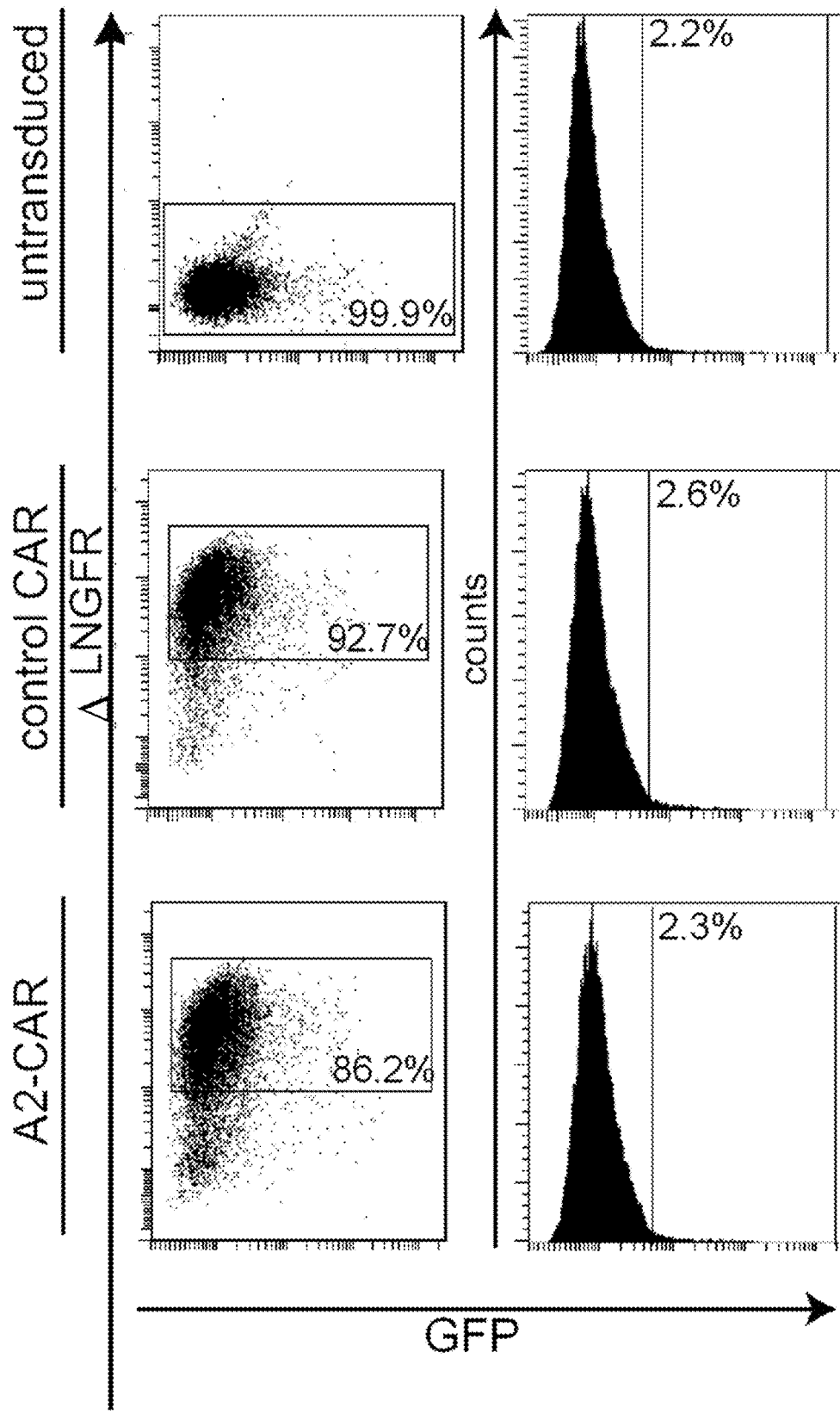
Figure 3C:
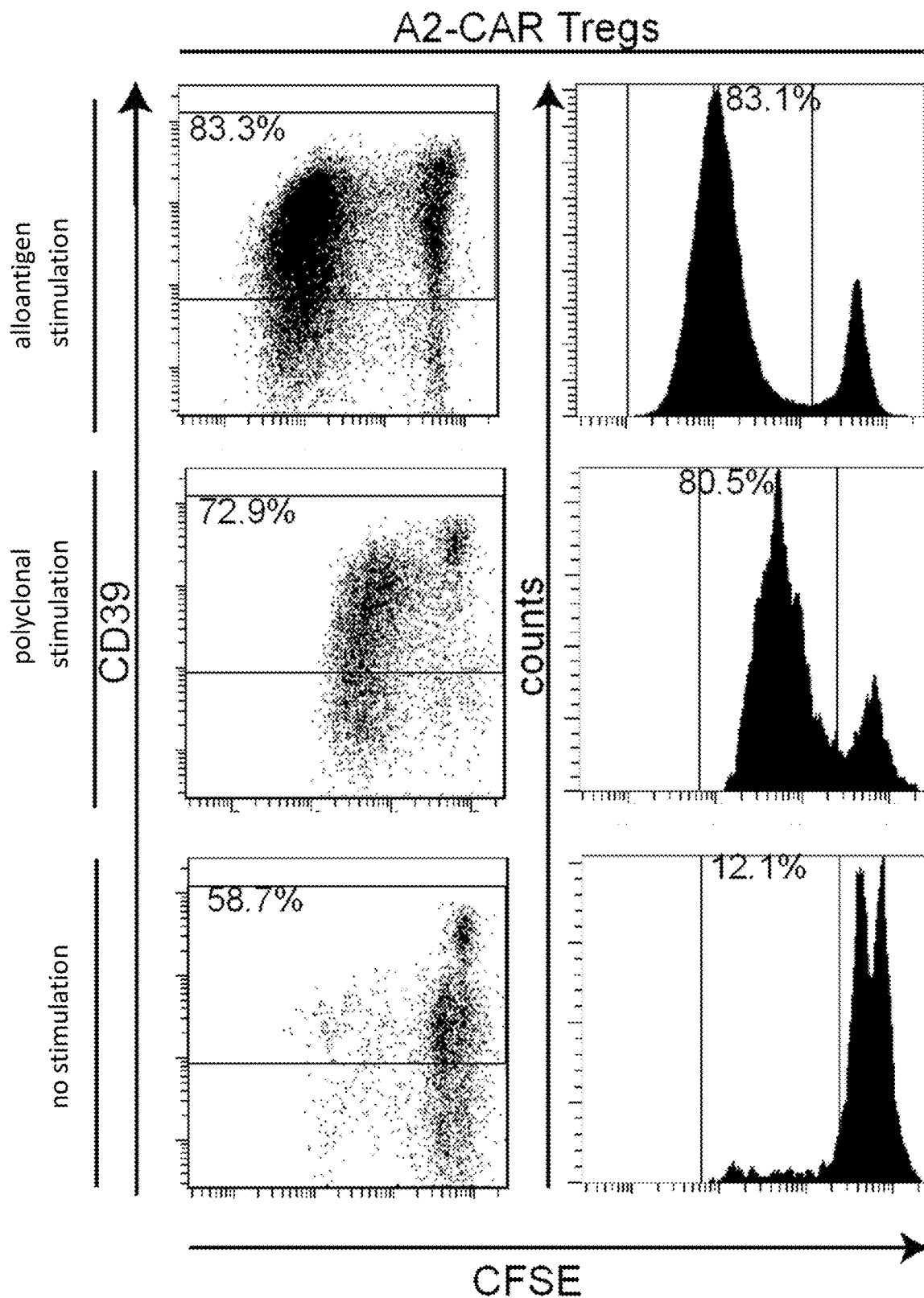
Figure 3D:
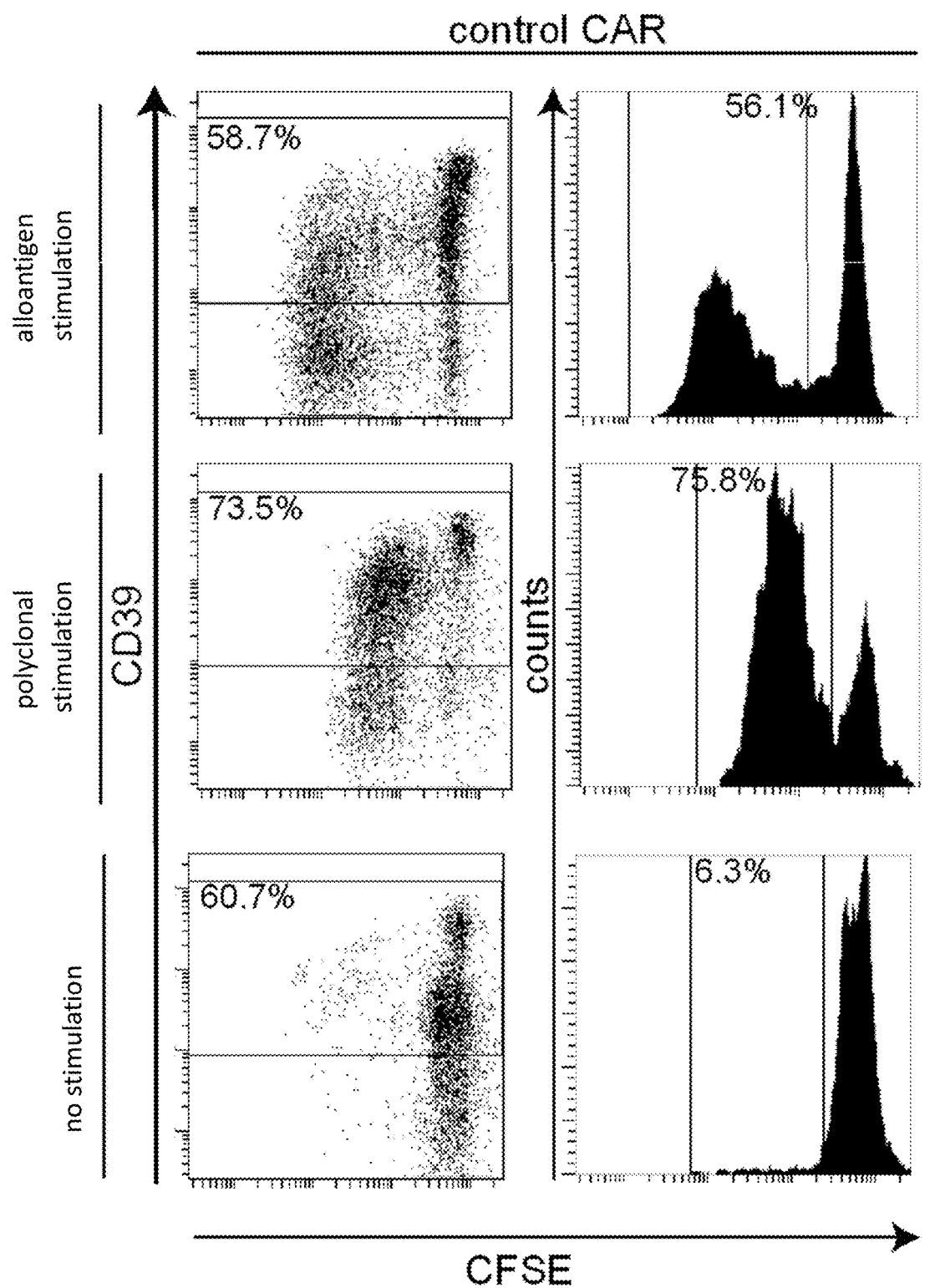
Figure 3E:
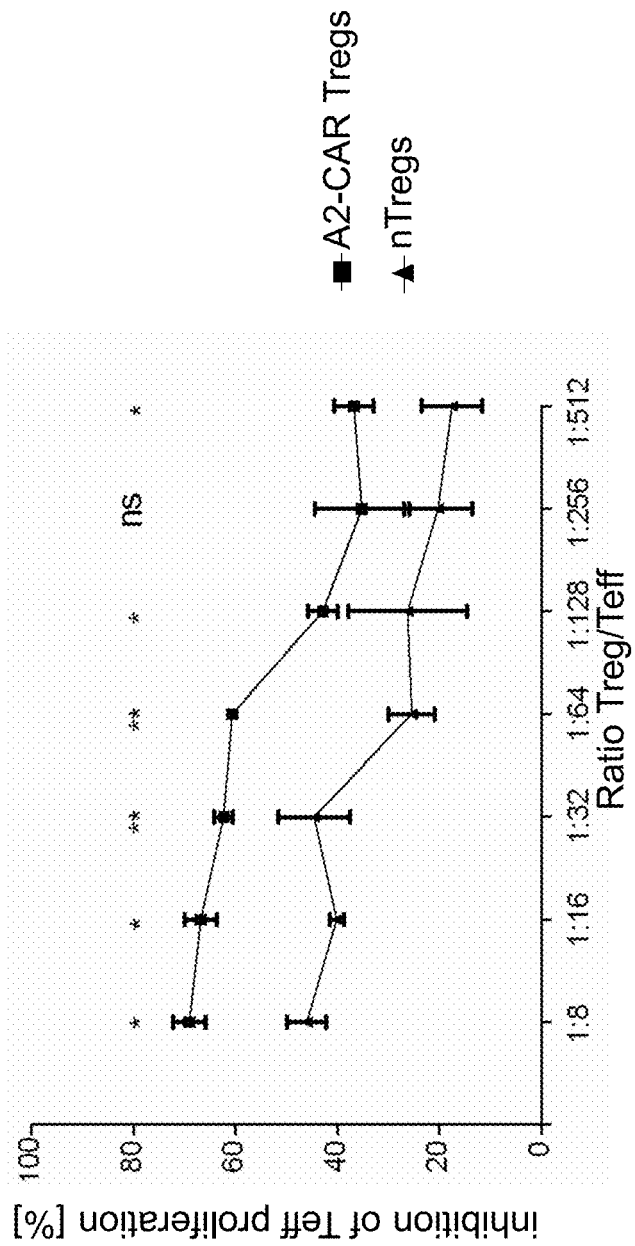
Figure 4A:
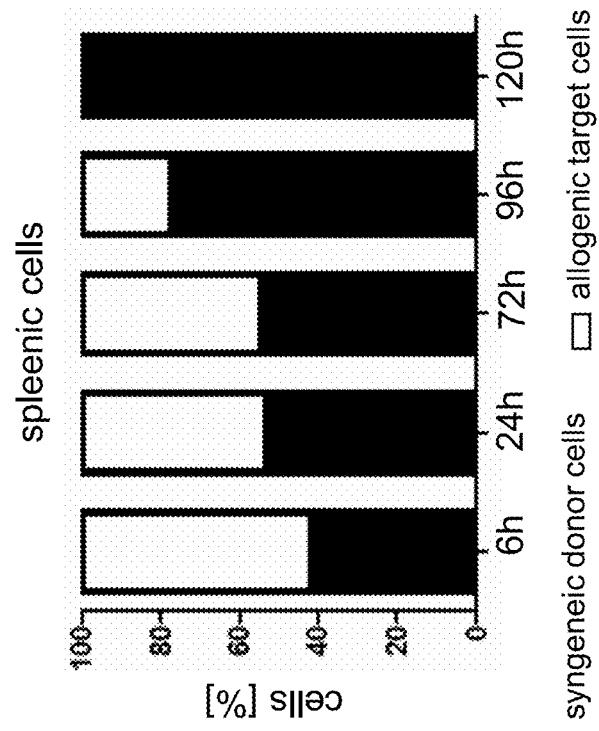
Figure 4B:
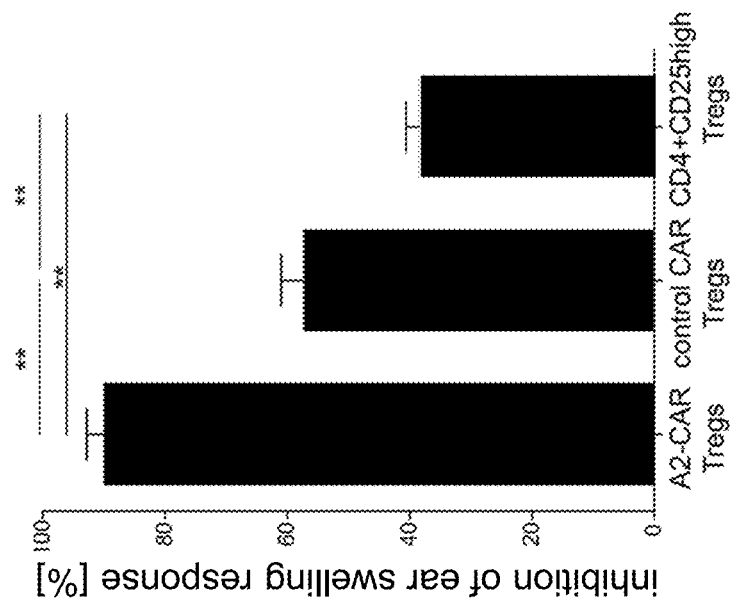
Figure 4C:
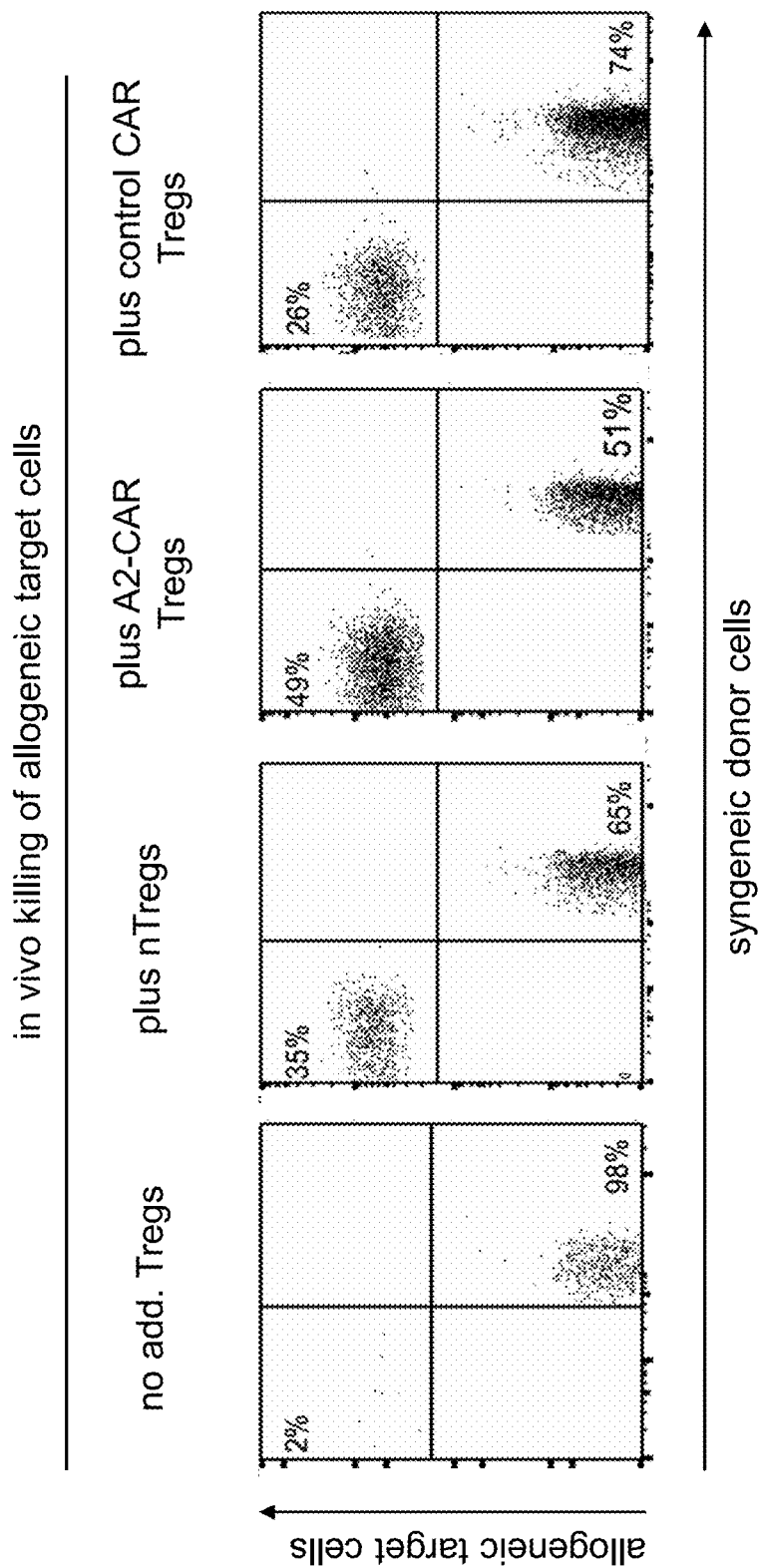
Figure 5A:
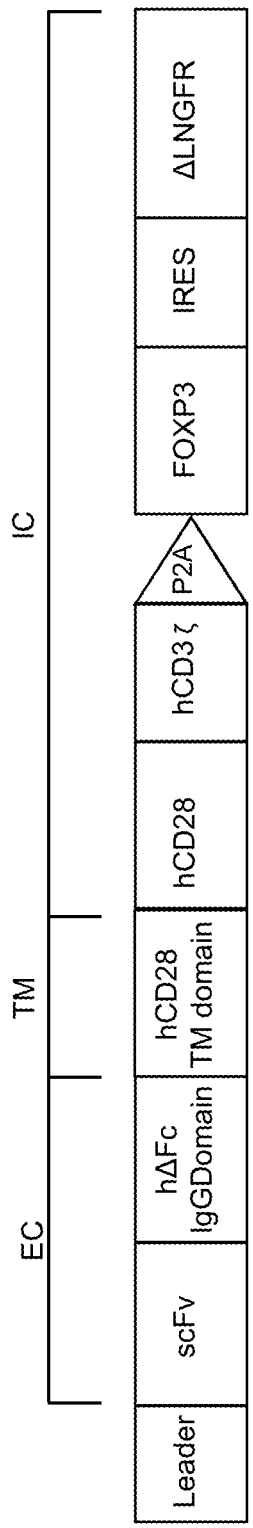
Figure 5B:
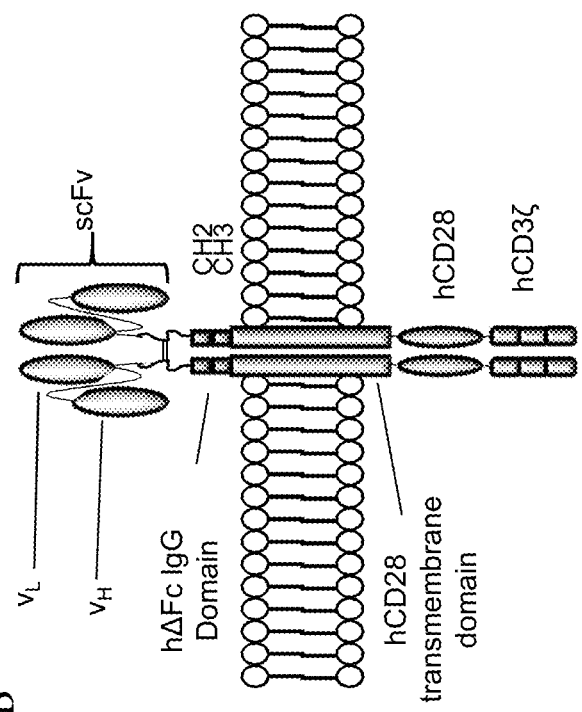
Figure 7A:
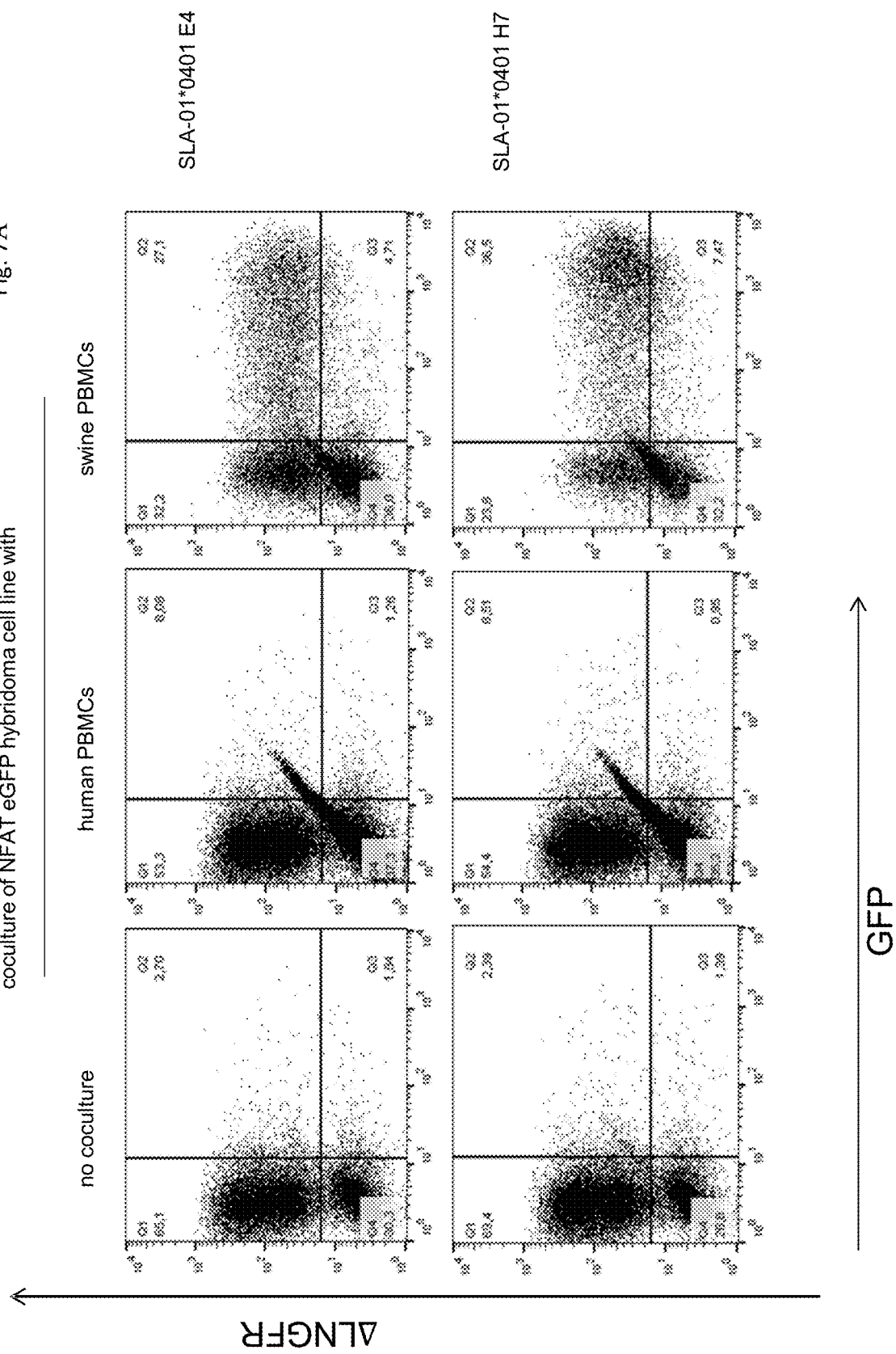

The invention is now described in greater detail by way of examples with reference to the figures, wherein FIG. 1A schematically shows a nucleic acid construct encoding a CAR-A*02 according to the invention suitable for retroviral transduction of Treg cells, FIG. 1B shows a schematic model of a CAR-A*02 arranged in a cell membrane, FIG. 1C shows FACS results indicating expression of CAR-A*02 and of a comparative control CAR on the surface of cells, FIG. 1D shows FACS results indicating that transduced Tregs express CAR-A*02 and specifically bind to HLA-A*02, FIG. 1E show FACS results indicating that Tregs transduced with CAR-A*02 do not bind to HLA-A*01, FIG. 1F shows FACS results for surface expression and specificity of the control CAR for PE, FIG. 2A shows FACS results for CCR7, CD39, CD45RO, CD45RA, CTLA-4 for non-transduced Treg cells and for Treg cells expressing CAR-A*02, FIG. 2B shows FACS results for STAT5 phosphorylation of CAR-A*02 expressing Treg cells and for non-transduced Treg cells, FIG. 2C shows a graph representing STAT5 phosphorylation in response to IL-2 concentration, FIGS. 3A and 3B show FACS results for activation of Treg cells expressing CAR-A*02 in response to stimulator cells, FIGS. 3C and 3D show FACS results for proliferation and CD39 expression of Treg cells expressing CAR-A*02 or a control CAR in response to specific stimulation, FIG. 3E shows a graph for the suppression of T-effector cells by Treg cells expressing CAR-A*02 at different cell ratios, *=P<0.05, **=P<0.01, FIG. 4a shows results of the suppressor activity in an in vivo MLR, FIG. 4b shows a graph of the analysis of an animal transplantation experiment using expression of the CAR-A*02 in Treg cells, and FIG. 4c shows FACS results of an animal transplantation experiment using expression of the CAR-A*02 in Treg cells, FIG. 5A schematically shows a nucleic acid construct encoding a CAR-SLA-01*0401 according to the invention, containing an optional fusion with P2A-FOXP3 and an additional IRES encoding ΔLNGFR as a reporter peptide, suitable for retroviral transduction of Treg cells, FIG. 5B shows a schematic model of a CAR-SLA-01*0401 arranged in a cell membrane, FIG. 5C shows FACS results of SC-1 cells for surface expression of CAR-SLA-01*0401, FIG. 5D shows FACS results of SC-1 cells for expression of FOXP3 after transduction with a nucleic acid construct encoding the fusion of FIG. 5a, FIG. 6 shows FACS results of human and porcine PBMC stained with labelled soluble scFv, FIGS. 7A and 7B show FACS results of hybridoma cells transduced to express CAR-SLA-01*0401, analysed for NFAT signalling.

Generally, the FACS results that are shown are representative of three independent experiments.

EXAMPLE 1: RETROVIRAL VECTOR ENCODING CAR-A*02 AND CELLS EXPRESSING CAR-A*02

The scFv domains for the CAR-A*02 were generated by affinity selection for HLA-A*02 using a phage display library expressing an anti-HLA-A*02 antibody. The anti-HLA-A*02 (nucleotide sequences accessible at EBI for heavy chain: AF163303; light chain: AF163304) was cloned from a patient who had developed A*02 reactive antibodies subsequent to blood transfusion.

As a result, antibodies could be isolated which had a significantly increased affinity for HLA-A*02 compared to the originally cloned anti-HLA-A*02 antibody.

The coding sequences for the scFv domains were cloned to generate a coding sequence for one fusion protein, from N-terminus to C-terminus containing the variable light chain, a linker, the variable heavy chain, the hCD8 hinge domain, the hCD6 transmembrane domain, the hCD28 intracellular signalling domain and the hCD3ζ intracellular signalling domain. The coding sequence was cloned between a 5'-LTR and a 3'-LTR of a retroviral vector, which between this coding sequence for the CAR-A*02 and the 3'-LTR additionally contained the coding sequence for the non-signalling surface molecule ΔLNGFR (truncated low-affinity nerve growth factor) as a reporter protein under the control of an IRES (internal ribosomal entry site) element acting as a promoter. In addition to its function as a reporter for expression of the CAR-A*02, such a reporter can be used for isolation of transduced cells, e.g. by affinity isolation using antibody specific for the reporter and coupled to a carrier, e.g. to magnetic beads.

For transduction, the nucleic acid sequence encoding CAR-A*02 was cloned into a gamma-retroviral LTR-driven expression vector.

The reporter ΔLNGFR was detected by flow cytometry using anti-CD271 antibody (C40-1457, Becton Dickinson).

For introduction of nucleic acid sequences encoding the CAR-A*02, a reporter, e.g. ΔLNGFR, were contained in a retroviral vector, producing viral particles containing the vector as described by Galla et al., Nuc. Ac. Res. 39, 1721-1731 (2009). After isolation of Treg cells, which are considered nTreg cells, these were stimulated with plate-bound anti-CD3 antibody (OKT-3, 5 µg/mL) and soluble anti-CD28 antibody (CD28.2, obtained from BioLegend, 5 µg/mL) in complete medium for 48 h. Prior to transduction, protamine sulfate (4 µg/mL, obtained from Sigma) was added to the Treg cultures. Treg cells were spin-infected with retroviral particles encoding CAR-A*02 or the control CAR specific for PE at 31° C. at 700×g for 1.5 h.

After transduction with the expression vector for the control CAR, SC-1 cells could be immunologically stained for ΔLNGFR by anti-CD271 antibody and stained for scFv using anti-IgG-Fab (obtained from Jackson Lab.), demonstrating surface expression of the control CAR and recognition of PE by the control CAR. Although the SC-1 cells do not express either FOXP3 or B220, they stain positive with a PE-conjugated antibody.

Human Treg cells were isolated from human PBMC using FACS with the following antibody combinations: anti-CD8 (HIT8a, obtained from BioLegend), anti-CD4 (RPA-T4, obtained from Becton Dickinson), anti-CD25 (M-A251, obtained from Becton Dickinson), anti-CD127 (hIL-7R-M21, obtained from Becton Dickinson), resulting in isolation of CD8⁻ CD4⁺ C25$^{high}$, CD8⁻ CD4⁺ C25$^{high}$ CD127$^{low}$ Tregs with a purity of at least 90%. The PBMC preparation was produced by density gradient centrifugation over Ficoll-Paque Plus (obtained from GE Healthcare) from different HLA-typed healthy donors after ethical approval and individual written informed consent.

Treg cells were transduced as described by Galla et al., Nuc. Ac. Res. 39, 1721-1731 (2009). Generally, all T-cell cultures and all T-cell related assays were performed in complete medium (RPMI 1640 GlutaMax-I (obtained from Gibco), supplemented with 10% fetal bovine serum (FBS) (obtained from Gibco), 1% penicillin and streptomycin (obtained from Biochrom), 0.05 mM (3-mercaptoethanol (obtained from Gibco), 20 mM HEPES (obtained from Gibco), 1% sodium pyruvate (obtained from Gibco) and 500 IU/mL IL-2 (Proleukin, obtained from Novartis) in humidified incubators at 37° C. and 5% $CO_2$. All cell lines were tested negative for mycoplasma.

FIG. 1A shows the arrangement of the nucleic acid construct of the CAR-A*02 including the coding sequence for the reporter ΔLNGFR under the control of an IRES element flanked by a 5'-LTR and a 3'-LTR of the gamma-retroviral vector. Generally, expression of a membrane bound protein in a Treg cell, e.g. under the control of an IRES linked to the coding sequence for the CAR-A*02, preferably in a viral vector, can be used for isolation of genetically manipulated Treg cells by affinity isolation directed to the membrane bound protein. An example for such a membrane bound protein is the ΔLNGFR.

FIG. 1B shows a model of the CAR-A*02 with its transmembrane domain spanning a cell membrane and the scFv arranged on the outer cell surface and the intracellular signalling domains arranged within the cytoplasm.

Membrane-anchored expression of the fusion protein on the surface of cells was tested using transduction of hybridoma cells. In short, hybridoma cells were transduced with the retroviral vectors encoding a CAR-A*02 or the negative control fusion protein. Stimulation of the transduced hybridoma cells was by contact with various HLA-A*02 positive or HLA-A*02 negative human PBMC (peripheral blood mononuclear cells). Co-culture was for 20 h with transduced hybridoma cells and irradiated (30 Gy). For specific staining of ΔLNGFR, an anti-CD271 antibody, C40-1457 (obtained from Becton Dickinson) was used, for specific staining of the CAR-A*02, the monoclonal antibody (mAb) anti-IgG-F(ab) (obtained from Jackson Labs) was used. Analysis was generally made by flow cytometry using a flow cytometer FACSCalibur (Becton Dickinson) or a LSRII (Becton Dickinson) using the FACSDiva software and FlowJo Software (Tree Star Inc.). For statistical analysis, the GraphPad Prism version 5.0 was used.

FIG. 1 shows expression and localisation of the reporter ΔLNGFR on the surface of the transduced hybridoma cells in original hybridoma cells (untransduced), staining for ΔLNGFR (control CAR) only, and staining for CAR-A*02 (A2-CAR). The results show that both the reporter ΔLNGFR and the CAR-A*02 were expressed on the surface of the transduced hybridoma cells.

Treg cells (CD4⁺ CD25$^{high}$ CD127$^{low}$) isolated from a HLA-A2*-negative person (HLA-A*02 neg donor) were transduced by the retroviral vector to express the CAR-A*02 and the reporter ΔLNGFR. For staining, HLA I tetramers displaying a hepatitis C virus peptide (HLA-A1-CMV Pentamer, obtained as pp65 from ProImmune) were used.

The FACS results of FIG. 1D show that transduced cells were stained with the HLA A*0201 (A*0201, obtained from Beckman coulter Immunomics, San Diego, USA) tetramers.

The FACS results of FIG. 1E show that the Treg cells from a HLA-A2*-positive person (HLA-A*02 pos donor), transduced to express the CAR-A*02 and the reporter ΔLNGFR, did not stain with A*01 tetramers.

The results of FIG. 1 show that the CAR-A*02 is expressed on the surface of transduced Treg cells, and that it specifically recognizes the HLA-A*02 tetramers, e.g. not recognizing HLA-A*01 tetramers. Further, it was found that the specific staining by the A*02 tetramers was independent of the peptide bound to the A*02 tetramer.

As a negative control CAR, a fusion protein containing an scFv specific for phycoerythrin (PE) in the place of the scFv specific for HLA-A*02, but otherwise identical, was encoded in the same expression vector. For determining surface expression and specificity of the control CAR, SC-1 cells, foetal mouse embryo cells which lack host-range restrictions for murine leukemia viruses (ATCC CRL-1404) were transduced according to Noyan et al., Cancer gene therapy 19, 352-357 (2012). The specificity of the control CAR for phycoerythrin (PE) was assessed by the use of several PE-conjugated proteins and PE-conjugated antibodies: murine B220-PE (RA3-6B2, obtained from Caltag), murine Foxp3-PE and murine Foxp3-PacBlue (FJK-16s, obtained from eBioscience), using the eBioscience Fix/Perm Kit for intracellular Foxp3 staining according to the manufacturer's instructions.

The FACS results of FIG. 1F show that the negative control CAR is expressed on the surface of cells and recognizes PE.

The phenotype of Treg cells that express the CAR-A*02 was analysed using Treg cells obtained from HLA-A*02 negative donors in order to prevent activation of the CAR-A*02 by the Treg cells themselves after transduction. This situation approximates the situation in a HLA-A*02 negative recipient. It was found that the transduction did essentially not affect the nTreg phenotype, with similar levels of effector molecules CTLA-4 and CD39 displayed in CAR-A*02-transduced Treg cells and in non-transduced nTreg cells, and similar percentages of CD45RA+ naïve Treg cells and similar expression of CCR7 were needed for homing the cells to secondary lymphoid organs. For staining, the antibodies anti-CD39 (A1, obtained from BioLegend), anti-CD45RA (HI100, obtained from Becton Dickinson), anti-CD45RO (UCHL1, obtained from BioLegend), anti-CCR7 (3D12, obtained from Becton Dickinson), anti-CTLA-4 (BNI3, obtained from Becton Dickinson), anti-FoxP3 (PCH101, obtained from eBioscience) were used. FIG. 2A shows these FACS results. The same phenotype was found for Treg cells transduced with the PE-specific control CAR.

STAT5 phosphorylation was measured using FACS (method as described in Long et al., Diabetes, 407-415 (2010) using anti-pSTAT5 antibody (pY694, 47/SAT5) obtained from Becton Dickinson) at different doses of IL-2 for Treg cells transduced with CAR-A*02 and non-transduced nTregs from the same experiment. The FACS results are depicted in FIG. 2B, showing that both these Treg cells showed high levels of STAT5 phosphorylation already under the low doses of IL-2 necessary for survival of nTreg in culture. The Treg cells transduced with CAR-A*02 showed a higher baseline and a slightly higher maximum STAT5 phosphorylation level in comparison to non-transduced cells. The graph of FIG. 2C compares STAT5 phosphorylation levels in relation to IL-2 doses. No defects in IL-2 signalling were observed. These results show that transduction of Treg cells to express CAR-A*02 did not significantly affect STAT5 phosphorylation, indicating no impairment of homing ability of these transduced cells.

For analysis of the function of CAR-A*02-transduced cells, T-cell hybridomas stably expressing a reporter construct containing an NFAT-sensitive IL-2 promoter to control GFP expression were transduced with the CAR-A*02. For detection of CAR expression in FACS analysis, the reporter ΔLNGFR was detected, NFAT stimulation was detected as expression of GFP (green fluorescent protein).

As shown in FIGS. 3A and 3B, it was found that CAR-A*02-transduced cells (A2-CAR) did not show any NFAT activation nor the associated expression of GFP after transduction, but NFAT activation and GFP expression were strongly up-regulated by co-culture with HLA-A*02+ PBMC acting as stimulator cells but not in response to HLA-A*02-PBMC. The non-transduced (untransduced) T-cell hybridomas and the cells that were transduced with the ΔLNGFR (control CAR) did not show a reaction to HLA-A*02 positive nor to HLA-A*02 negative PBMC stimulator cells. This result shows that the CAR-A*02 according to the invention is capable of signal transduction necessary to activate NFAT. As the hybridomas do not express any endogenous T-cell receptor (TCR), the signal transduction that was observed is entirely caused by the signalling of the CAR-A*02.

The differentiation between signalling by CAR or by TCR will be more difficult when HLA-A*02 negative donor Treg cells are transduced with the CAR-A*02, because 8 to 12% of these nTreg cells will have a TCR that also recognizes HLA-A*02. Therefore, the CAR-A*02 was tested against a wide panel of human PBMC presenting various MHC I and MHC II alleles, using expression in the T-cell hybridomas containing the reporter construct. The analysis was by flow cytometry of GFP expression. The results showed that the CAR-A*02 (HLA-A2 CAR) upon expression in the hybridomas recognized all HLA-A*02 positive donor samples without any cross-reactivity with HLA-A*02 negative blood samples. For comparison, the control CAR specific for PE (irrelevant CAR) was used. The results are summarized in the following table, wherein the individual HLA-A and HLA-B are indicated in each row for the numbered samples (Human PBMCs) and X designates GFP expression:

| Human PBMCs | HLA-A | | HLA-B | | HLA-A2 CAR | irrelevant CAR |
|---|---|---|---|---|---|---|
| 1  | 2  |    | 23 | 44 | X | — |
| 2  | 3  | 24 | 7  | 13 | — | — |
| 3  | 1  | 24 | 8  | 40 | — | — |
| 4  | 1  |    | 8  | 57 | — | — |
| 5  | 3  | 24 | 7  | 13 | — | — |
| 6  | 2  | 24 | 35 | 37 | X | — |
| 7  | 24 | 31 | 13 | 51 | — | — |
| 8  | 2  |    | 51 | 62 | X | — |
| 9  | 2  |    | 60 | 61 | X | — |
| 10 | 2  | 3  | 38 | 44 | X | — |
| 11 | 3  | 25 | 7  | 18 | — | — |
| 12 | 2  | 25 | 35 | 44 | X | — |
| 13 | 11 | 23 | 27 | 44 | — | — |
| 14 | 2  | 31 | 62 | 27 | X | — |
| 15 | 3  |    | 7  | 62 | — | — |
| 16 | 3  | 30 | 7  | 13 | — | — |
| 17 | 2  | 24 | 7  | 62 | X | — |
| 18 | 3  |    | 35 |    | — | — |
| 19 | 2  | 3  | 13 | 18 | X | — |
| 20 | 1  | 2  | 27 | 60 | X | — |

The hybridoma cells expressing the control CAR after co-culture with the blood samples did not express GFP (−) for any of the HLA. This demonstrated the high specificity of the CAR-A*02 according to the invention for HLA-A*02, showing low or absent unspecific or off-target activity.

The effect of activating the CAR-A*02 according to the invention when it is expressed in human HLA-A*02 negative Treg cells was tested using HLA-A*02 positive PBMC as stimulator cells. Proliferation of Treg cells expressing the CAR-A*02 was analysed based on a CFSE dilution assay, for which the Treg cells were labelled with CFSE (5 mM, obtained from Invitrogen). For the HLA-A*02 negative Treg cells expressing the CAR-A*02 polyclonal stimulation was used by co-cultivation with irradiated (30 Gy) HLA-A*02 positive PBMC (stimulator cells) which were also contacted with 5 mM APC cell proliferation dye (eFluor 670, obtained from eBioscience) in a 1:4 ratio. For the human HLA-A*02 negative Treg cells transduced to express the control CAR (specific for PE), stimulation was by anti-CD3/anti-CD28 directed to the TCR. Detection of CD39 using anti-CD39 antibody (A1, BioLegend) was measured for Treg activation, and CFSE was detected for proliferation. For comparison, FACS analysis of CFSE dilution of proliferating cells was made. The FACS results are depicted in FIGS. 3C and 3D, showing that the CAR-A*02 was strongly activated by HLA-A*02 positive PBMC, resulting in a strong proliferation and up-regulation of the CD39 effector molecule. This effect was much stronger than in the activated Treg cells expressing the control CAR. The Treg cells expressing the control CAR are likely activated via their allospecific TCR, as this is found on up to 12% of all nTreg cells. The up-regulation of CD39 was also found upon activation using the combination of anti-CD3 and anti-CD28 antibodies, which act on the TCR. These data indicate that the Treg cells expressing the CAR-A*02 according to the invention can be activated equally well via the CAR-A*02 or via the TCR.

It is assumed that the high proliferative capacity of the Treg cells expressing the CAR-A*02 according to the invention after transfer into a patient supports their effect, e.g. their niche filling capability.

EXAMPLE 2: SUPPRESSOR ACTIVITY OF CAR-A*02 IN VITRO

The suppressor activity of Treg cells expressing the CAR-A*02 of Example 1 was tested by assaying the suppression of an allogeneic mixed lymphocyte reaction (MLR) directed against HLA-A*02 positive CD1c stimulator cells. The responder cells were CFSE labelled (5 mM) isolated CD4+CD25− effector T-cells that were co-cultured with isolated HLA-A*02 CD1c+ cells in the presence of various ratios of syngeneic HLA-A1 CD4$^+$ CD25$^+$CD127$^{low}$ Treg (nTreg) cells or syngeneic Treg cells expressing the CAR-A*02 for five days. Suppression of syngeneic effector T-cell proliferation was calculated on the basis of the ratios Treg/Teff via a CFSE dilution assay. For comparison, non-transduced nTreg cells from the same transduction experiment were used.

The result is depicted in FIG. 3E, showing that the Treg cells expressing the CAR-A*02 (A2-CAR Tregs) much more potently inhibited the proliferation of allospecific effector T-cells compared to the non-transduced Treg cells (nTregs). The Treg cells expressing the CAR-A*02 were more potent suppressors at almost all ratios of the CAR-A*02-expressing Treg/effector T-cells tested. Even at a ratio of 1:64 of CAR-A*02-expressing Treg/effector T-cells (Ratio Treg/Teff), inhibition of over 60% was observed, demonstrating the strong suppressive activity conferred by the CAR-A*02 fusion protein.

For analysis of the consequences of signalling in Treg cells by CAR-A*02, a transcriptome analysis comprising 1149 genes was made by deep sequencing in non-activated and CAR-A*02 expressing Treg cells and compared to the results obtained for non-transduced Treg cells. The CAR-A*02 expressing Treg cells (CD4$^+$ CD25$^{high}$ CD127$^{low}$) were activated with irradiated (30 Gy) HLA-A*02+ PBMC as stimulator cells by co-culture for 36 h. As a control, non-transduced Treg cells were left untreated or were stimulated via their TCR by the combined anti-CD3/anti-CD28 antibodies, for 48 h. After stimulation, RNA was isolated using the MicroRNeasy kit (obtained from Qiagen), quality and integrity of total RNA was measured on an Agilent Technologies 2100 Bioanalyser. An RNA sequencing library was generated from 100 ng total RNA using TruSeq RNA Sample Prep kits v2 (obtained from Illumina) for mRNA purification followed by ScriptSeq v2 RNA Seq Library Preparation kit (obtained from Epicentre) according to the manufacturer's protocols. The libraries were sequenced on an Illumina HiSeq2500 device using TruSeq SBS kit v3-HS (50 cycles, single ended run) with an average of $3\times10^7$ readings per RNA sample. Readings were aligned to the reference genome hg19 using the open source short read aligner STAR with default settings. The readings per gene after alignment were made by the feature.count function of the R package termed Rsubread. For log2 transformation of raw count data followed by data normalisation and statistical determination of differentially expressed genes, the R package termed edgeR was used.

It was found that the CAR-A*02 transduced Treg cells and the non-transduced Treg cells had a very similar pattern of activated and down-regulated transcripts, supporting the notion that signalling via the CAR-A*02 leads to comparable transcriptional profiles in Treg cells as signalling via the TCR. The activation of the CAR-A*02 or of the TCR, respectively, resulted in drastic changes of the transcriptional profiles compared to the non-activated state, but the transcriptional profiles of both activated states were similar to one another. An analysis of specific genes that are involved in Treg cell function and their homing revealed subtle differences. The CAR-A*02 activated Treg cells expressed higher amounts of IL-4, IL-5 and IL-10 but slightly lower transcript numbers of CTLA4 and IL-2R. These decreased transcript levels had no apparent consequence for CTLA4 protein expression (FIG. 2A), nor for IL-2 signalling (FIG. 2B, FIG. 2C).

EXAMPLE 3: SUPPRESSOR ACTIVITY OF CAR-A*02 IN VIVO

As an example for suppressor activity in vivo, humanized non-obese diabetic (NOD)-RAG1$^{null}$IL2γ$^{null}$ (NRG) mice, non-reconstituted, received $5\times10^4$ CD4$^+$ CD25$^+$CD127$^{low}$ human Treg cells from HLA-A*02 negative donors, which Treg cells were transduced with the retroviral vector encoding the CAR-A*02 according to Example 1, or the same Treg cells transduced with the control CAR (specific for PE) of Example 1, or the non-transduced Treg cells. As an example for transplanted tissue, mice were injected into each ear pinnae with admixed $5\times10^5$ irradiated syngeneic HLA-A*01 PBMC and allogeneic irradiated HLA-A*02 PBMC as an in vivo MLR.

These experiments were performed in a blinded manner. For determining the suppressor activity, ear swelling was measured using a spring-loaded digital thickness gauge. FIG. 5A shows the results of the ear swelling, calculated as the difference between ear thickness prior to injection and 24 h after injection, with each value related to the ear swelling observed in the other ear of the animal that had not been injected with Treg cells as an internal control.

The result is depicted in FIG. 5A, showing a significantly stronger inhibition of the allogeneic mixed lymphocyte reaction for the Treg cells expressing CAR-A*02 (A2-CAR Tregs) in comparison to Treg cells expressing the control CAR (control CAR Tregs) and in comparison to the non-transduced Tregs (CD4+CD25high Tregs).

In another experiment, the suppressor activity was analysed in immune reconstituted NRG mice. Currently, testing transplant rejection in such mice is difficult, because in immunocompetent mice, an allogeneic skin transplant is rejected within 10 d, while a similar rejection in humanized NRG mice does not occur before day 30 after transplantation. At this late point in time, xenospecific graft-versus-host responses already become evident after immune reconstitution. In order to avoid other effects than the GvHD reaction, a stringent rejection model was used in which allogeneic transplanted cells are completely rejected by day 5 after transplantation by injection. The use of injected allogeneic transplant cells has the additional advantage that homing of Treg cells to transplanted tissues should not play a major role because the immune response is initiated in the spleen, therefore avoiding possible effects of the perturbed homing in humanized mice.

As Treg cells, CD4$^+$ CD25$^+$CD127$^{low}$ human Treg cells transduced with CAR-A*02 according to Example 1, or the same Treg cells transduced with the control CAR (specific for PE) of Example 1, or the non-transduced Treg cells were used. Immune reconstitution was monitored by FACS 14 d after reconstitution by expression of human CD8 and human CD4 in peripheral blood samples from the mandibular vein. Animals with no perceptible reconstitution of human CD8 and CD4 T cells were excluded from experiments. On day 14 after immune reconstitution, mice were injected i.v. with $5\times10^5$ syngeneic PBMC labelled with CFSE and $5\times10^5$ HLA-A*02 PBMC as allogeneic positive target cells which were labelled with APC proliferation dye. Simultaneously, different animals received different Treg cells at $5\times10^4$, which were Treg expressing CAR-A*02 (plus A2-CAR Tregs) or control CAR (plus control CAR Tregs) or non-transduced (plus nTregs). Five days after injection, mice were sacrificed and blood and splenic cells were analysed for allogeneic targets and syngeneic donor cells, and compared to those obtained in animals that did not receive Treg cells (no add. Tregs). The labelling of syngeneic and allogeneic cells allowed to assess the relative killing of allogeneic target cells in the animals as both cell populations were injected at a 1:1 cell ratio.

Representative FACS results are depicted in FIG. 5C, showing that in immunocompetent mice allogeneic target cells were no longer detected after 120 h after transplantation, corresponding to the fast rejection of allogeneic tissue in non-humanized mice. The injection of Tregs expressing the control CAR or of non-transduced Tregs had a small effect in preventing killing of allogeneic target cells, the transfer of Treg cells expressing a CAR-A*02 completely prevented the rejection of allogeneic target cells.

EXAMPLE 4: EXPRESSION OF CAR-SLA-01*0401

Fusion proteins CAR-SLA-01*0401, containing scFv having specificity for the porcine SLA-01*0401, were expressed from a nucleic acid construct according to FIG. 5a, encoding from 5' to 3' adjacent to one another a leader peptide for secretion (SEQ ID NO: 25), an scFv specific for the MEW class I, a hΔFc IgG domain as a preferred hinge, the hCD28 TM domain as a transmembrane domain, hCD28, hCD3ζ, P2A, FOXP3, an IRES, and ΔLNGFR as a reporter. Therein, the P2A is arranged such that following expression, FOXP3 is cleaved off and can translocate into the nucleus. The scFv and the hinge form the extracellular (EC) portion, The TM domain forms the transmembrane portion, and the hCD28 and hCD3ζ as well as the optional P2A and FOXP3 form the intracellular (IC) portion. Also, the reporter ΔLNGFR is intracellular. The reporter is expressed from the same nucleic acid construct, indicating its presence, but as a separate protein.

FIG. 5B in a model shows the arrangement of the CAR-SLA-01*0401 with its transmembrane domain spanning a cell membrane and the scFv arranged on the outer cell surface and the intracellular signalling domains arranged within the cytoplasm.

Sc1 cells were transduced separately with nucleic acid constructs encoding fusion proteins according to FIG. 5a of a leader, an scFv, the hΔFc IgG domain of SEQ ID NO: 20, the hCD28 TM domain fused to the hCD28 signalling domain and fused to hCD3ζ of SEQ ID NO: 21, with the optional P2A-hFOXP3 of SEQ ID NO: 22. The reporter ΔLNGFR of SEQ ID NO: 23 was transcribed from an IRES (internal ribosomal entry site). The scFv was one selected from SEQ ID NO: 16 to SEQ ID NO: 19, having specificity for the porcine SLA-01*0401.

FACS results for staining of non-transduced cells for comparison (untransduced) and for transduced cells expressing the CAR-SLA-01*0401 containing the scFv E4 of SEQ ID NO: 17 (SLA-01*0401 E4), the scFv H7 of SEQ ID NO: 19 (SLA-01*0401 H7) or the scFv C5 of SEQ ID NO: 16 (SLA-01*0401 C5) are shown in FIG. 5c with staining for the reporter ΔLNGFR and staining with an anti-IgG-Fab, and in FIG. 5d with staining for FOXP3 and staining with an anti-IgG-Fab. The results show surface expression of the hinge formed by the hΔFc IgG domain and concurrent expression of the reporter and concurrent expression of FOXP3, demonstrating that the fusion protein is located in the cell membrane with the extracellular domains on the outside and the signalling domains on the inside.

The cross-reactivity of the CAR-SLA-01*0401 to human cells was tested using soluble scFv antibodies of E4 (SEQ ID NO: 17), H7 (SEQ ID NO: 19), C5 (SEQ ID NO: 16), and F11 (SEQ ID NO: 18). The soluble scFv contained an additional C-terminal $His_6$-Tag not given in the sequences.

FIG. 6 shows the FACS results for human PBMC and porcine PBMC, respectively, after incubation with the labelled scFv. The results show no cross-reactivity of the scFv with human PBMC and labelling of the porcine PBMC with each of the scFv.

For analysis of the function of CAR-SLA-01*0401-transduced cells, T-cell hybridomas stably expressing a reporter construct containing an NFAT-sensitive IL-2 promoter to control GFP expression were transduced with the CAR-SLA-01*0401. For detection of CAR expression in FACS analysis, the reporter ΔLNGFR was detected, NFAT stimulation was detected as expression of GFP (green fluorescent protein).

As shown in FIGS. 7A and 7B, it was found that CAR-SLA-01*0401-transduced cells, containing the scFv domain E4, H7, F11 or C5, did not show any NFAT activation nor the associated expression of GFP after transduction, but NFAT activation and GFP expression were strongly up-regulated by co-culture with porcine PBMC acting as stimulator cells but not in response to human PBMC. This result shows that the CAR-SLA-01*0401 according to the invention is capable of signal transduction necessary to activate NFAT in the presence of porcine cells. As the hybridomas do not express any endogenous T-cell receptor (TCR), the signal transduction that was observed is entirely caused by the signalling of the CAR-SLA-01*0401.

EXAMPLE 5: SUPPRESSOR ACTIVITY OF CAR-SLA-01*0401 IN VIVO

As an example for a solid allogeneic transplant tissue, porcine islet cells were transplanted into mice as recipients. The most commonly used approach to study allogeneic or xenogeneic islet function in preclinical models is to monitor blood glucose levels after islet transplantation into hyperglycemic humanized mice. Presently, animals were treated with streptozozocin (STZ) to render the mice hyperglycemic by the destruction of insulin producing islet cells. Those hyperglycemic mice were transplanted with isolated adult pig islets under the kidney capsule in order to replace destructed murine islet cells. 14 days following the transplantation, animals were reconstituted with human PBMCs (xenogeneic to transplanted pig islets) with additional and without additional (control group) porcine Treg cells transduced to express a CAR-SLA-01*0401. Islet function and cell viability were monitored via blood glucose level of experimental animals. Those data are compared with immunofluorescence data from explanted kidneys at final stage of experiments to explore accumulation of CAR Tregs in islet cell clusters.

The invention claimed is:

1. Fusion protein comprising a single-chain variable fragment antibody domain (scFv), a hinge, a transmembrane domain, an intracellular hCD28 signalling domain and an intracellular hCD3ζ (hCD3 zeta) signalling domain forming a chimeric antigen receptor having specificity for HLA-A*02 (CAR-A*02) or having specificity for SLA-01*0401 (CAR-SLA-01*0401) for use in the treatment of HvG disease in a patient, the single-chain variable fragment antibody domain (scFv) having an amino acid sequence which is selected from the group consisting of SEQ ID NO: 1 to SEQ ID NO: 12 or SEQ ID NO: 16 to SEQ ID NO: 19.

2. Fusion protein according to claim 1, wherein the hinge and the transmembrane domain have an amino acid sequence of SEQ ID NO: 13, the hCD28 signalling domain has an amino acid sequence of SEQ ID NO: 14, and the hCD3ζ (hCD3 zeta) signalling domain has an amino acid sequence of SEQ ID NO: 15.

3. Fusion protein according to claim 1, wherein the hinge is a hΔFc IgG domain having an amino acid sequence of SEQ ID NO: 20.

4. Fusion protein according to claim 1, wherein the hinge and the transmembrane domain, which is a CD8 transmembrane domain, have an amino acid sequence of SEO ID NO: 13, the hCD28 signalling domain has an amino acid sequence of SEQ ID NO: 14, and the hCD3 ζ domain has an amino acid sequence of SEQ ID NO: 15, or the hCD28 signalling domain including the hCD3ζ signalling domain have an amino acid sequence of SEQ ID NO: 21.

5. Fusion protein according to claim 1, expressed in a CD4$^+$CD25$^+$CD127$^{low}$ HLA-A*02 negative human regulatory T (Treg) cell.

6. Fusion protein according to claim 1, comprising or consisting of, from N-terminal to C-terminal, one scFv domain having an amino acid sequence selected from the group consisting of SEQ ID NO: 1 to SEQ ID NO: 12, a hinge and a transmembrane domain having an amino acid sequence of SEQ ID NO: 13, a hCD28 signalling domain having an amino acid sequence of SEQ ID NO: 14, and a hCD3ζ (hCD3 zeta) signalling domain having an amino acid sequence of SEQ ID NO: 15.

7. Fusion protein according to claim 1, comprising or consisting of, from N-terminal to C-terminal, one scFv domain having an amino acid sequence selected from the group consisting of SEQ ID NO: 16 to SEQ ID NO: 19, a hΔFc IgG domain as a hinge having an amino acid sequence of SEQ ID NO: 20, a hCD28 transmembrane domain and a hCD28/hCD3 signalling domain having an amino acid sequence of SEQ ID NO: 21.

8. Fusion protein according to claim 1, expressed from a nucleic acid sequence encoding the fusion protein with optionally an additional N-terminal secretory leader peptide.

9. Fusion protein according to claim 1, expressed from a nucleic acid sequence encoding the fusion protein with an additional N-terminal secretory leader peptide and an additional C-terminal P2A-hFOXP3 having an amino acid sequence of SEQ ID NO: 22.

10. Fusion protein according to claim 8, wherein the leader peptide has an amino acid sequence selected from SEQ ID NO: 24 and SEQ ID NO: 25.

11. Fusion protein according to claim 1, wherein the fusion protein provides suppressor activity to a CD4$^+$CD25$^+$CD127$^{low}$ HLA-A*02 negative human regulatory T (Treg) cell in the presence of HLA-A*02 positive solid tissue or in the presence of SLA-01*0401 positive solid tissue.

12. Fusion protein according to claim 10, wherein the fusion protein provides for homing capability to secondary lymphoid organs in a CD4$^+$CD25$^+$CD127$^{low}$ HLA-A*02 negative human regulatory T (Treg) cell.

13. Process for providing a human regulatory T (Treg) cell having suppressor activity in the presence of HLA-A*02 positive solid tissue or in the presence of SLA-01*0401 positive solid tissue, comprising the steps of
  a. isolating from a blood sample CD4$^+$CD25$^+$CD127$^{low}$ human regulatory T (Treg) cells to produce isolated Treg cells,
  b. introducing a nucleic acid sequence encoding and expressing a fusion protein according to one of claims 1 to 12 into the isolated Treg cells to produce Treg cells expressing the fusion protein, wherein the Treg cells expressing the fusion protein are not expanded in in vitro culture.

14. Process according to claim 13, wherein isolating the human regulatory T cells is isolating HLA-A*02 negative human regulatory T cells.

15. Process for providing a human regulatory T (Treg) cell having suppressor activity in the presence of SLA-01*0401 positive solid tissue, comprising the steps of
  a. isolating from a blood sample CD4$^+$CD25$^+$CD127$^{low}$ human regulatory T (Treg) cells to produce isolated Treg cells,
  b. introducing a nucleic acid sequence encoding and expressing a fusion protein according to one of claims 1 to 12 into the isolated Treg cells to produce Treg cells expressing the fusion protein, wherein the Treg cells expressing the fusion protein are not expanded in in vitro culture.

16. Process according to claim 13, wherein the nucleic acid sequence is comprised in a retroviral vector that is packaged in a retroviral particle and is introduced into the isolated Treg cells by transduction.

17. Process according to claim 13, wherein following step b., the Treg cells are kept in culture for 24 h, followed by isolating Treg cells expressing the fusion protein.

18. Process according to claim 17, wherein the Treg cells are kept in culture in a medium containing low dose IL-2, which medium does not contain an agent stimulating expansion of Treg cells.

* * * * *